United States Patent [19]

Hodges et al.

[11] Patent Number: 5,210,211
[45] Date of Patent: May 11, 1993

[54] 4-(1H-PYRROL-1-YL) IMIDAZOLES WITH ANGIOTENSION II ANTAGONIST ACTIVITY

[75] Inventors: John C. Hodges; John G. Topliss, both of Ann Arbor, Mich.

[73] Assignee: Warner-Lambert Company, Morris Plains, N.J.

[21] Appl. No.: 883,023

[22] Filed: May 19, 1992

Related U.S. Application Data

[63] Continuation-in-part of Ser. No. 719,271, Jun. 21, 1991, abandoned.

[51] Int. Cl.⁵ .................. C07D 403/04; C07D 233/88; C07D 233/90
[52] U.S. Cl. ............................. 548/314.7; 548/326.5
[58] Field of Search .................... 548/336, 337, 343

[56] References Cited

U.S. PATENT DOCUMENTS 4,820,843  4/1989  Aldrich et al. ............... 548/252

FOREIGN PATENT DOCUMENTS 0253310  1/1988  European Pat. Off. .
0401030  12/1990  European Pat. Off. .
9100277  1/1991  World Int. Prop. O. .

OTHER PUBLICATIONS

*Hypertension*, 18[Suppl. II]:II60–II64 (1991).
*Japan. J. Pharmacol.*, 52:541–552 (1990).
*FASEB*, 52(4):A869 (1990).

*Primary Examiner*—Patricia L. Morris
*Attorney, Agent, or Firm*—Elizabeth M. Anderson

[57] ABSTRACT

Novel substituted 4-(1-H-pyrrol-1-yl)imidazoles are disclosed as well as methods of preparing them, pharmaceutical compositions containing them, and methods of using them. Novel intermediates useful in the preparation of the compounds of the invention are also disclosed and synthetic methods for preparing the novel intermediates. The compounds are useful as antagonists of angiotensin II and thus are useful in the control of hypertension, hyperaldosteronism, congestive heart failure, glaucoma, vascular smooth muscle proliferation associated with atherosclerosis, and with postsurgical vascular restenosis.

1 Claim, No Drawings

4-(1H-PYRROL-1-YL) IMIDAZOLES WITH ANGIOTENSION II ANTAGONIST ACTIVITY

This application is a continuation-in-part of Ser. No. 07/719,271, filed Jun. 21, 1991, now abandoned.

BACKGROUND OF THE INVENTION

The present invention relates to novel substituted derivatives of 4-(1H-pyrrol-1-yl)imidazoles which are useful as pharmaceutical agents, to methods for their preparation, to pharmaceutical compositions which include the compounds and a pharmaceutically acceptable carrier, and to pharmaceutical methods of treatment as well as the use of these agents as diagnostic tools. The novel compounds of the present invention are antagonists of angiotensin II (AII) useful in controlling hypertension, hyperaldosteronism, congestive heart failure, atherosclerosis, postsurgical vascular restenosis, renal failure, and glaucoma in mammals.

The enzyme renin acts on a blood plasma $\alpha_2$-globulin, angiotensinogen, to produce angiotensin I, which is then converted by angiotensin converting enzyme to AII. The latter substance is a powerful vasopressor agent which has been implicated as a causative agent for producing high blood pressure in various mammals, such as rats, dogs, and humans. Angiotensin II has also been found to stimulate vascular hyperplasia as reported by W. Osterrieder, et al (*Hypertension* 18[suppl II]:II60-II64, 1991); H. Azuma, et al (*Jpn. J. Pharmacol.* 52(4):541-552, 1990); and S. Laporte, et al (*FASEB* 5(4), Part I: A869, 1991). The compounds of this invention inhibit the action of AII at its receptors on target cells and thus prevent the increase in blood pressure produced by this hormone-receptor interaction. By administering a compound of the instant invention to a species of mammal with hypertension due to AII, the blood pressure is reduced. The compounds of the invention are also useful for the treatment of congestive heart failure, hyperaldosteronism, atherosclerosis, postsurgical vascular restenosis, and glaucoma.

European Patent Application 0253310 discloses angiotensin II receptor blocking imidazoles of the formula

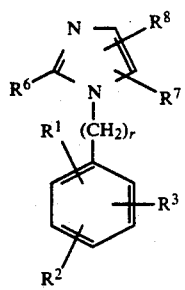

I

European Patent Application 0291969 disclose tetrazole intermediates to antihypertensive compounds

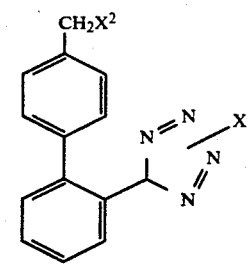

European Patent Application 401030 discloses substituted imidazo-fused seven-member ring heterocycles of Formulae I and Ia

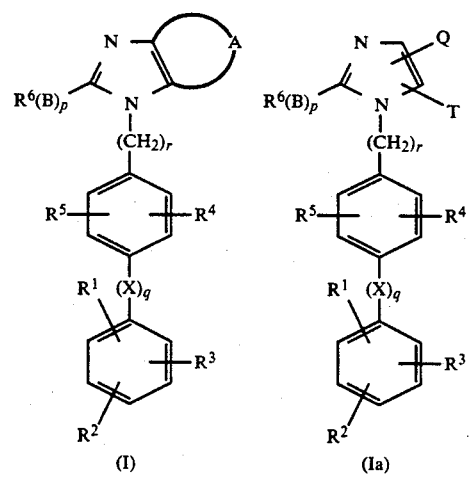

which are useful as angiotensin II antagonists.

WO 91/00277 discloses substituted imidazoles useful as angiotensin II blockers

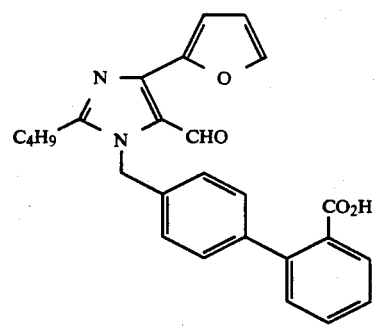

However, the compounds disclosed in the above references do not disclose or suggest the novel combination of structural variations found in the compounds of the present invention described hereinafter.

SUMMARY OF THE INVENTION

The present invention is a compound of Formula I

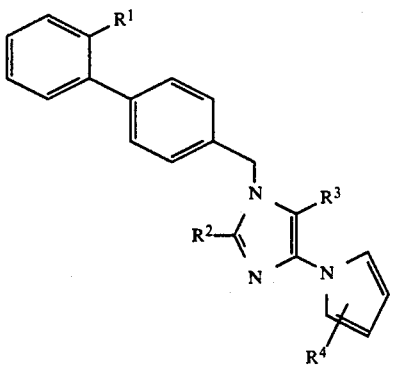

or a pharmaceutically acceptable salt thereof wherein $R^1$, $R^2$, $R^3$, and $R^4$ are as described below.

Preferred compounds of the instant invention are those of Formula I wherein $R^1$ is —COOH or

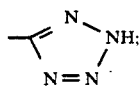

$R^2$ is
 —$_nC_3H_7$ or
 —$_nC_4H_9$;

$R^3$ is
 —H,
 —COOR$^5$
 —CN,
 —CHO,
 —CH$_2$OH,
 (CH$_2$)$_n$CO$_2$R$^5$,
 —CH=CHCO$_2$R$^5$, or
 —CH=C(CH$_3$)CO$_2$R$^5$ wherein $R^5$ is hydrogen or a straight or branched alkyl of from one to four carbon atoms and n is 1 or 2; $R^4$ is absent or is one or two substituents attached to the pyrrole ring selected from:
2-CH$_3$,
2-CO$_2$R$^5$,
3-CO$_2$R$^5$,
2-CH$_2$OH,
3-CH$_2$OH,
2-Cl,
2-Br,
2-CONHOH,
3-CONHOH,
2-COCF$_3$,
2-COCCl$_3$,
2-CH(OH)CF$_3$,
2-CH(OH)CCl$_3$,
2,5-(Cl)$_2$,
2,5-(Br)$_2$, and
2,5-(CH$_3$)$_2$.

More preferred compounds of the instant invention are those of Formula I wherein $R^1$ is

$R^2$ is
 —$C_4H_9$ or
 —$_nC_3H_7$;

$R^3$ is
 —H,
 —CN,
 —CO$_2$H,
 CO$_2$CH$_3$,
 —CH$_2$OH; and $R^4$ is absent or is one or two substituents attached to the pyrrole ring selected from:
2-CO$_2$CH$_3$,
2-COCF$_3$,
2-CO$_2$H,
2-CH(OH)CF$_3$,
2,5-(Cl)$_2$, and
2,5-(CH$_3$)$_2$.

Yet still more preferred compounds of the instant invention are selected from the following list of compounds:

1) 2-butyl-5-cyano-4-(1H-pyrrol-1-yl)-1-[(2'-(1H-tetrazol-5-yl)biphen-4-yl)methyl]-1H-imidazole, 2) 5-cyano-2-propyl-4-(1H-pyrrol-1-yl) 1-[(2,-(1H-tetrazol-5-yl)biphen-4 yl)methyl]-1H-imidazole, 3) 2-butyl-4-(1H-pyrrol-1-yl)-1-[(2'-(1H-tetrazol-5-yl)biphen-4-yl)methyl]-1H-imidazole-5-carboxylic acid, 4) 2-propyl-4-(1H-pyrrol-1-yl)-1-[(2'-(1H-tetrazol-5-yl)biphen-4-yl)methyl]-1H-imidazole-5-carboxylic acid, 5) 2-butyl-4-(1H-pyrrol-1-yl)-1-[(2'-(1H-tetrazol-5-yl)biphen-4-yl)methyl]-1H-imidazole, 6) ethyl 2-butyl-4-(1H-pyrrol-1-yl)-1-[(2'-(1H-tetrazol-5-yl)biphen 4-yl)methyl]-1H-imidazole-5-carboxylate, 7) methyl 2-butyl-4-(1H-pyrrol-1-yl)-1-[(2'-(1H-tetrazol-5-yl)biphen-4-yl)methyl]-1H-imidazole-5-carboxylate, 8) 2-butyl-5-(hydroxymethyl)-4-(1H-pyrrol-1-yl)-1-[(2'-(1H-tetrazol-5-yl)biphen-4-yl)methyl]-1H-imidazole, 9) 5-cyano-4-[2-(1-oxo-2,2,2-trifluoroethyl)-1H-pyrrol-1-yl]-2 propyl-1-[(2'-(1H-tetrazol-5-yl)biphen-4-yl)-methyl]-1H-imidazole, 10) 5-cyano-4-[2-(1-hydroxy-2,2,2-trifluoroethyl)-1H-pyrrol-1-yl]-2-propyl-1-[(2'-(1H-tetrazol-5-yl)biphen-4-yl)methyl]-1H-imidazole, 11) methyl 1-[5-cyano-2-propyl-1-[(2'-(1H-tetrazol-5-yl)-biphen-4-yl)methyl]-1H-imidazol-4-yl]-1H-pyrrole-2-carboxylate, 12) 1-[5-cyano-2-propyl-1-[(2'-(1H-tetrazol-5-yl)biphen-4 yl)methyl]-1H-imidazol-4-yl]-1H-pyrrole-2-carboxylic acid, 13) 5-cyano-4-(2,5 dichloro-1H-pyrrol-1-yl)-2-propyl-1-[(2'-(1H-tetrazol-5-yl)biphen-4-yl)methyl]-1H-imidazole, 14) methyl 4-(2,5-dichloro-1H-pyrrol-1-yl)-2-propyl-1-[(2'-(1H-tetrazol-5-yl)biphen-4-yl)methyl]-1H-imidazole-5-carboxylate, 15) 2-cyclopropyl-4-(2,5-dimethyl-1H-pyrrol-1-yl)-1-[(2'-(1H-tetrazo-5-yl)biphen-4-yl)methyl]-1H-imidazole-5-carboxylic acid, 16) methyl 2-cyclopropyl-4-(2,5-dimethyl-1H-pyrrol-1-yl)-1-[(2'-(1H-tetrazol-5-yl)biphen-4-yl)methyl]-1H-imidazole-5-carboxylate, 17) methyl 4-(2-propyl-5-methyl-1H-pyrrol-1-yl)-2-propyl-1-[(2'-(1H-tetrazol-5-yl)biphen-4-yl)methyl]-1H-imidazole-5-carboxylate, 18) 4-(2-propyl-5-methyl-1H-pyrrol 1 yl)-2-propyl-1-[(2'-(1H-tetrazol-5-yl)biphen-4-yl)methyl]-1H-imidazole-5-carboxylic acid,
19) 4-(2,5-dimethyl-1H-pyrrol-1-yl)-2-propyl-1-[(2'-(1H-tetrazol-5-yl)biphen-4-yl)methyl]-1H-imidazole-5-carboxaldehyde,
20) methyl (E)-3-[4-(2,5-dimethyl-1H-pyrrol-1-yl)-2-propyl-1-[[2'-(1H-tetrazol-5-yl)biphen-4-yl]methyl]-1H-imidazol-5-yl]-2-propenoate,
21) (E)-3-[4-(2,5-dimethyl-1H-pyrrol-1-yl)-2-propylo-1-[[2'-(1H-tetrazol-5-yl)biphen-4-yl]methyl]-1H-1H-imidazol-5-yl]-2-propenoic acid,
22) 4-(3-carboxyethyl-1H-pyrrol-1-yl)-2-propyl-1-[[(2'-(1H-tetrazol-5-yl)biphen-4-yl)methyl]-1H-imidazole-5-carboxylic acid,
23) methyl 4-(3-carboxyethyl-1H-pyrrol-1-yl)-2-propyl-1-[(2'-(1H-tetrazol-5-yl)biphen-4-yl)methyl]-1H-imidazole-5-carboxylate,
24) 4-(3-carboxy-1H-pyrrol-1-yl)-2-propyl-1-[(2'-(1H-tetrazol-5-yl)biphen-4-yl)methyl]-1H-imidazole-5-carboxylic acid,
25) ethyl (E)-3-[4-(1H-pyrrol-1-yl)-2-propyl-1-[[2'-(1H-tetrazol-5-yl)biphen-4-yl]methyl]-1H-imidazol 5-yl]-2-propenoate,
26) (E)-3-[4-(1H-pyrrol-1-yl)-2-propyl-1-[[-2'-(1H-tetrazol-5-yl)biphen-4-yl]methyl]-1H-imidazol-5-yl]-2-propenoic acid,
27) methyl 4-(2,5-dimethyl-1H-pyrrol-1-yl)-2-propyl-1-[(2'-(1H-tetrazol-5-yl)biphen-4-yl)methyl]-1H-imidazole-5-carboxylate,
28) 4-(2,5-dimethyl-1H-pyrrol-1-yl) 2-propyl-1-[(2'-(1H-tetrazol-5-yl)biphen-4-yl)methyl]-1H-imidazole-5-carboxylic acid,
29) 2-propyl-4-(-1H-pyrrol-1-yl)-1 [(2'-(1H-tetrazol-5-yl)biphen-4-yl)methyl]-1H-imidazole-5-carboxaldehyde,
30) 4-(2,5-dimethyl-1H-pyrrol-1-yl)-5-(hydroxymethyl)-2-propyl-1-[(2'-(1H-tetrazol-5-yl)biphen-4-yl)methyl]-1H-imidazole,
31) 5-cyano-4-(2,5-dimethyl-1H-pyrrol-1-yl)-2-propyl-1-[(2'-(1H-tetrazol-5-yl)biphen-4-yl)methyl]-1H-imidazole,
32) methyl 4-(3-carboxymethyl-2-methyl-1H-pyrrol-1-yl)-2-propyl-1-[(2'-(1H-tetrazol-5-yl)biphen-4-yl)methyl]-1H-imidazole-5-carboxylate,
33) 4-(3-carboxymethyl-2-methyl-1H-pyrrol-1-yl) 2-propyl-1-[(2'-(1H-tetrazol-5-yl)biphen-4-yl)methyl]-1H-imidazole-5-carboxylic acid,
34) 4-(3 carboxy-2-methyl-1H-pyrrol-1-yl)-2-propyl-1-[(2'-(1H-tetrazol-5-yl)biphen-4-yl)methyl]-1H-imidazole-5-carboxylic acid,
35) 4-[2-(1-oxo-2,2,2-trifluoroethyl)-1H-pyrrol-1-yl]-2-propyl-1-[(2'-(1H-tetrazol-5-yl)biphen-4-yl)methyl]-1H-imidazole-5-carboxylic acid,
36) 2-butyl-4-[2-(1-oxo-2,2,2-trifluoroethyl)-1H-pyrrol-1-yl]-1-[(2'-(1H-tetrazol-5-yl)biphen-4-yl)methyl]-1H-imidazole-5-carboxylic acid,
37) methyl 4-[2-(1 oxo-2,2,2-trifluoroethyl)-1H-pyrrol-1-yl]-2-propyl 1-[(2'-(1H-tetrazol-5-yl)biphen-4-yl)methyl]-1H-imidazole-5-carboxylate,
38) methyl 2-butyl-4-[2-(1-oxo-2,2,2-trifluoroethyl)-1H-pyrrol-1-yl]-1-[(2'-(1H-tetrazol-5-yl)biphen-4-yl)methyl]-1H-imidazole-5-carboxylate,
39) 1-[5-carboxy-2-propyl-1-[(2'-(1H-tetrazol-5-yl)biphen-4-yl)methyl]-1H-imidazol-4-yl]-1H-pyrrole-2-carboxylic acid
40) ethyl (E)-2-methyl-3-[4-(1H-pyrrol-1-yl)-2-propyl-1-[[2'-(1H-tetrazol-5-yl)biphen-4-yl]methyl]-1H-imidazol-5-yl]-2-propenoate,
41) (E)-2-methyl-3-[4-(1H-pyrrol-1-yl)-2-propyl-1[[-2'-(1H-tetrazol-5-yl)biphen-4-yl]methyl]-1H-imidazol-5-yl]-2-propenoic acid, and
42) 4-(2,5 dichloro-1H-pyrrol-1-yl)-2-propyl-1-[(2'-(1H-tetrazol-5-yl)biphen-4-yl)methyl]-1H-imidazole-5-carboxylic acid.

Novel intermediates useful in the preparation of compounds of the instant invention are:
1) 4-amino-2-butyl-5-cyanoimidazole,
2) 4-amino-5-cyano-2-propylimidazole,
3) 2-butyl-5-cyano-4-(1H-pyrrol-1-yl)imidazole,
4) 5-cyano-2-propyl-4-(1H-pyrrol-1-yl)imidazole,
5) ethyl 2-butyl-4-(1H-pyrrol-1-yl)imidazole-5-carboxylate,
6) methyl 2-butyl-4-(1H-pyrrol-1-yl)imidazole,
7) 2-butyl-5-(hydroxymethyl)-4-(1H-pyrrol-1-yl)imidazole-5-carboxylate,
8) 5-cyano-4-[2-(1-oxo-2,2,2-trifluoroethyl)-1H-pyrrol-1-yl]-2-propylimidazole,
9) methyl 1-(5-cyano-2-propylimidazol-4-yl)-1H-pyrrole-2-carboxylate,
10) 5-cyano-4-(2,5-dichloro-1H-pyrrol-1-yl)-2-propylimidazole.
11) methyl 4-[2-(1-oxo-2,2,2-trifluoroethyl)-1H-pyrrol-1-yl]-2-propylimidazole-5-carboxylate,
12) methyl 2-butyl-4-[2-(1-oxo-2,2,2-trifluoroethyl)-1H-pyrrol-1-yl]imidazole-5-carboxylate,
13) 5-cyano-4-(2,5-dichloro-1H-pyrrol-1-yl)-2-propylimidazole,
14) methyl 2-cyclopropyl-4-(2,5-dimethyl-1H-pyrrol-1-yl)imidazole-5-carboxylate,
15) methyl 4-(2-propyl-5-methyl-1H-pyrrol-1-yl)-2-propylimidazole-5-carboxylate,
16) 4-(2,5-dimethyl-1H-pyrrol-1-yl)-2-propylimidazole-5-carboxaldehyde,
17) methyl 4-(3-carboxyethyl-1H-pyrrol-1-yl)-2-propyl-imidazole-5-carboxylate,
18) methyl 4-(2,5-dimethyl-1H-pyrrol-1-yl)-2-propylimidazole-5-carboxylate,
19) 2-propyl-4-(1H-pyrrol-1-yl)-imidazole-5-carboxaldehyde,
20) 5-(hydroxymethyl)-2-propyl-4-(1H-pyrrol-1-yl)imidazole,
21) 2-butyl-5-(hydroxymethyl)-4-(1H-pyrrol-1-yl)imidazole,
22) 5-cyano-4-(2,5-dimethyl-1H-pyrrol-1-yl)-2-propylimidazole,
23) methyl 4-(2-methyl-3-carboxymethyl-1H-pyrrol-1-yl)-2-propylimidazole-5-carboxylate,
24) methyl 2-butyl-4-[2-(1-oxo-2,2,2-trifluoroethyl)-1H-pyrrol-1-yl]imidazole-5-carboxylate,
25) methyl 2-propyl-4-(2,5-dichloro-1H-pyrrol-1-yl)-imidazole-5-carboxylate,
26) 5-(hydroxymethyl)-2-propyl-4-(1H-pyrrol-1-yl)imidazole,
27) methyl 4-amino-2-cyclopropylimidazole-5-carboxylate,
28) 5-(hydroxymethyl)-2-propyl-4-(2,5-dimethyl-1H-pyrrol-1-yl)imidazole,
29) methyl (E)-3-[4-(2,5-dimethyl-1H-pyrrol-1-yl)-2-propylimidazol-5-yl]-2-propenoic acid, Angiotensin II mediates a variety of responses in various tissues, including contraction of vascular smooth muscle, excretions of salt and water from kidney, release of prolactin from pituitary, stimulation of aldosterone secretion from adrenal gland, and possible regulation of cell growth in both cardiac and vascular tissue As antagonists of angiotensin II, the compounds of the instant invention are useful in controlling hypertension, hyperaldosteronism, congestive heart failure, and vascular smooth muscle proliferation associated with atherosclerosis and post surgical vascular restenosis in mammals. Additionally, antihypertensive agents as a class have been shown to be useful in lowering intraocular pressure. Thus, the other inventions are also useful in treating and/or preventing glaucoma.

One method of particular interest is a method of treating hypertension comprising administering to a host suffering therefrom a therapeutically effective amount of 4-[2-(1-oxo-2,2,2-trifluoroethyl)-1H-pyrrol-1-yl]-2-propyl-1-[(2'-(1H-tetrazol-5-yl)biphen-4-yl)methyl]-1H-imidazole-5-carboxylic acid, or the methyl ester thereof in unit dosage form.

The present invention is also a pharmaceutical composition for administering an effective amount of a compound of Formula I in unit dosage form in the treatment methods mentioned above.

Finally, the present invention is directed to methods for the preparation of a compound of Formula I and synthetic intermediates.

DETAILED DESCRIPTION OF THE INVENTION

The invention is of a compound of Formula

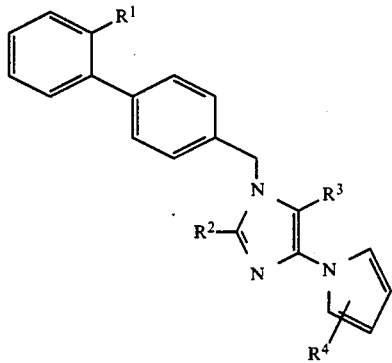

I or a pharmaceutically acceptable salt thereof wherein $R^1$ is —COOH, or

$R^2$ is
 —$C_2H_5$,
 —$nC_3H_7$,
 —$nC_4H_9$,
 —$nC_4H_9$,
 $CH_2CH=CH_2$,
 —$CH_2CH=CHCH_3$, or
 $CH_2CH_2CH=CH_2$;
$R^3$ is
 —H,
 —CN,
 —CHO,
 —$CH_2OH$,
 —$COOR^5$ $$-CH_2OCR^5\atop\|\atop O$$

—$(CH_2)_nCN$,
 —$(CH_2)_nCO_2R^5$,
 —$(CH_2)_nCONH_2$,
 —$(CH_2)_nCONHOH$, or
 $CH=CHCO_2R^5$,
 —$C=C(CH_3)CO_2R^5$
 wherein $R^5$ is hydrogen or a straight or branched alkyl of from one to four carbon atoms and n is 1 or 2; and
$R^4$ is absent or is one or two substituents attached to the pyrrole ring selected from:
 2-$CH_3$,
 2-$CH_2CH_3$,
 2-$CH_2CH_2CH_3$
 2-$CF_3$,
 2-$CO_2R^5$,
 2-CHO,
 2-$CH_2OH$,
 2-$CH_2OCR^5$, $$2\text{-}CH_2OCR^5,\atop\|\atop O$$

2-$NO_2$,
 2-Cl,
 2-Br,
 2-I,
 2$COCF_3$,
 2-$COCCl_3$,
 2-$CH(OH)CF_3$,
 2-$CH(OH)CCl_3$,
 2-$CONH_2$,
 2-$CONHOH$,
 3-$CH_3$,
 3-$CH_2CH_3$,
 3-$CF_3$,
 3-$CO_2R^5$,
 3-CHO,
 3-$CH_2OH$, $$3\text{-}CH_2OCR^5,\atop\|\atop O$$

3-$NO_2$,
 3-$CONH_2$,
 3-$CONHOH$,
 2-$CO_2R^5$-4-$NO_2$,
 2-$COCCl_3$-4-$NO_2$,
 2-$COCF_3$-4-$NO_2$,
 2-$CO_2R^5$-4-Cl,
 2-$COCCl_3$-4-Cl,
 2-$COCF_3$-4-Cl,
 2-$COCF_3$-4-Cl,
 2-$CO_2R^5$-4-Cl,
 2-$COCCl_3$-4-Cl,
 2-$COCF_3$-4-Cl,
 2-$COCF_3$-4-Cl,
 2-$CO_2R^5$-4-Br,
 2-$COCCl_3$-4-Br,
 2-$COCF_3$-4-Br,
 2-$CO_2R^5$-4-I,

2-COCCl$_3$-4-I,
2-COCCF$_3$-4-I,
2-NO$_2$-4-CO$_2$R$^5$,
2-Cl-4-CO$_2$R$^5$,
2-Br-4-CO$_2$R$^5$,
2-I-4-CO$_2$R$^5$,
2-CH$_3$-3-CO$_2$R$^5$,
2,5-(CH$_3$)$_2$,
2,5-COCF$_3$,
2,5-(CH$_2$CH$_3$)$_2$,
2-CH$_2$CH$_2$CH$_3$-5 CH$_3$,
2,5-(Cl)$_2$,
2,5-(Br)$_2$, and
2,5-(I)$_2$ wherein R$^5$ is hydrogen or a straight or branched alkyl of from one to four carbon atoms.

Certain compounds of the present invention can exist in unsolvated forms as well as solvated forms, including hydrated forms. In general, the solvated forms, including hydrated forms, are equivalent to unsolvated forms and are intended to be encompassed within the cope of the present invention.

Certain compounds of the present invention possess one or more chiral centers and each center may exist in the R(D) or S(L) configuration. The present invention includes all enantiomeric and epimeric forms as well as the appropriate mixtures thereof.

In the compounds of Formula I, the term "lower alkyl" means a straight or branched hydrocarbon radical having from one to six carbon atoms and includes, for example, methyl, ethyl, n propyl, isopropyl, n-butyl, sec-butyl, isobutyl, tert-butyl, n-pentyl, n-hexyl, and the like.

Halogen is fluorine, chlorine, bromine, or iodine.

The compounds of Formula I are capable of further forming both pharmaceutically acceptable acid addition and/or base salts. All of these forms are within the scope of the present invention.

Pharmaceutically acceptable acid addition salts of the compound of Formula I include salts derived from nontoxic inorganic acids such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, S. M., et al, "Pharmaceutical Salts," *Journal of Pharmaceutical Science* 66:1-19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediaunine, chloroprocaine, choline, diethanolamine, ethylenediamine, N-methylglucamine, and procaine (see, for example, Berge, S. M., et al., "Pharmaceutical Salts," Ibid.

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Compounds of Formula I may be prepared according to the syntheses outlined in Schemes I-VI. Although these schemes often indicate exact structures, the methods apply widely to analogous compounds of Formula I, given appropriate consideration to protection and deprotection of reactive functional groups by methods standard to the art of organic chemistry. The strategy for preparation of compounds of Formula I involves N(1) alkylation of a 4-(1H-pyrrol-1-yl)imidazole fragment with a biphenyl fragment. Schemes I, II, III, IV, and IVa deal with preparation of various 4-(1H-pyrrol-1-yl)imidazole fragments. Scheme V shows the synthesis of several biphenylmethyl halides and Scheme VI depicts the combination of the two fragments and subsequent manipulation to give compounds of Formula I. Additionally, many of the chemical modifications which are described for the N-unsubstituted 4-(1H-pyrrol-1-yl)imidazole fragments are also possible, and often preferable, once the biphenyl fragment is attached at N(1).

Scheme I and II detail methods for the preparation of 2-alkyl 4-(1H-pyrrol-1-yl)imidazoles. The key intermediate in both schemes is 5 which can be prepared by three routes. In the first method (Scheme I), reaction of an alkyl orthoester (1) with an aminonitrile (2) in a polar solvent such as methanol or ethanol affords the imino ether (3) which is treated in situ with methanolic ammonia. A cyclization reaction occurs to give 5. The second method (Scheme I) reacts an alkylimino ether (4) with an aminonitrile (2) in a polar solvent such as methanol or ethanol to give 5 in a single step. In those cases where the aminonitrile (2) and/or the alkylimino ether (4) are available as acid addition salts, it is necessary that at least one equivalent of a mild base such as potassium acetate, sodium acetate or the like be added for each equivalent of acid addition salt used in the reaction. The third method is detailed in Scheme II. In this route, an alkylimino ether (4) is reacted with an excess of aqueous cyanamide buffered (optimum pH 2.5-6.5) with dibasic sodium phosphate to afford the N cyanoalkylimino ether (7). The N-cyano-alkylimino ether (7) is further reacted in a polar solvent such as methanol or ethanol with an acid addition salt of a glycine ester in the presence of a base such as triethylamine to produce the N-(N'-cyanoalkyl imidoyl)-glycinate ester (8). Cyclization of (8) to the key intermediate (5) is effected by treatment with an alkoxide base such as sodium methoxide or sodium ethoxide and the like in a polar solvent. Finally, treatment of 5 prepared via Scheme I or Scheme II with 2,5-dimethoxy-tetrahydrofuran derivatives in buffered acetic acid at reflux converts the free amino group to a substituted or unsubstituted pyrrole, affording 6. Buffering of the acetic acid is best achieved by addition of 2-10 equivalents of either potassium or sodium acetate. This conversion of 5 to 6 is an example of the Paal-Knorr pyrrole synthesis which is well known to those skilled in the art of heterocyclic chemistry and has been reviewed in *The Chemistry of Heterocyclic Compounds*, E. C. Taylor, Editor, *Pyrroles* (Part 1), R. Alan Jones, Editor; John Wiley and Sons (1990), pp 206-294.

Selected examples of compound 6 wherein an ester group is located at the 5 position may be further modified to give additional 4-(1H-pyrrol-1yl)imidazoles according to Scheme 3. Reduction of 6 with a hydride reducing agent such as lithium aluminum hydride, lithium borohydride, and the like affords the alcohol, 9. Manganese dioxide oxidation of 7 gives the aldehyde 10. Knoevenagel condensation of malonic acid with 10 in refluxing piperidine affords the free acid 11a. Alteratively, 10 is converted to ester derivatives (11b) via the Wadsworth-Emmons reaction employing such reagents as, but not limited to, trimethylphosphonoacetate, triethylphosphoacetate, and tert-butyl diethylphosphonoacetate in polar solvents such as, tetrahydrofuran, acetonitrile, dimethylformamide, methanol and ethanol employing such bases as sodium hydride, sodium methoxide, potassium t butoxide, lithium diethylamide, and 1,8-diazabicyclo[5.4.0]non-5-ene to afford the appropriate ester of 11b.

Electrophilic reactions of pyrrole derivatives are described in great detail in *The Chemistry of Heterocyclic Compounds*, E. C. Taylor, Editor, *Pyrroles* (Part 1), R. Alan Jones, Editor; John Wiley and Sons (1990), pp 329-497. Schemes IV and IVa show examples of such electrophilic substitutions pertinent to this invention. Treatment of a compound such as 6 (Scheme IV) with common electrophilic reagents including $HNO_3$/acetic anhydride, N-chlorosuccinimide, trichloroacetyl chloride, N-bromosuccinimide or trifluoroacetic anhydride gives compounds of formula 12 with predominantly 2-substitution of nitro, chloro, trichloroacetyl, bromo and trifluoroacetyl groups on the pyrrole ring. Nitration also gives some of the 3 nitro isomer. Use of two equivalents of N chloro or N-bromosuccinimide gives the 2,5-dichloro and 2,5-dibromopyrrole groups at the 4 position of 12.

Similarly, treatment of compounds of formula 6a (Scheme IVa), wherein the pyrrole ring already has an electron withdrawing group at the 2-position, with common electrophilic reagents affords compounds of formula 12a with a 2,4 substitution pattern on the pyrrole ring. Finally, treatment of compounds of formula 6b (Scheme IV), wherein the pyrrole ring already has an electron withdrawing group at the 3-position, with common electrophilic reactions affords compounds of formula 12b with a 2,4 substitution pattern complementary to the pattern seen on 12a.

The synthesis of the biphenyl fragments (Scheme V) is based on methods of A. Suzuki, et al, *Syn. Commun.* 11(7):513-519 (1981). The cross-coupling of o-bromobenzonitrile 13 or methyl o-bromobenzoate 13a with p-tolylboronic acid 14 (F. R. Bean and J. R. Johnson, *J. Amer. Chem. Soc.* 54:4415-4424 (1934), European Patent 0470795) is effected by heating in dimethoxyethane or toluene in the presence of a palladium catalysts such as tetrakis(triphenylphosphine) palladium(O) and two equivalents of an aqueous 2M solution of sodium carbonate to afford the unsymmetrical biphenyls, 15 and 15a. The biphenylnitrile 15 is then converted to 16 by a two-step process. Thus, 15 is treated with trimethyltin azide in refluxing toluene solution to construct the tetrazole ring by a 1,3-dipolar cycloaddition. Subsequent replacement of the trimethyltin group on the newly constructed tetrazole ring is accomplished by treatment with triphenylmethyl chloride in pyridine solution, affording 16. Both the trityl protected biphenyltetrazole 16 and the biphenylester 15a are brominated at their respective benzylic positions by treatment with N-bromosuccinimide and a catalytic quantity of a radical initiator such as 2,2-azobis(2-methylpropionitrile) or benzoyl peroxide in refluxing carbon tetrachloride to afford the key intermediates 17 and 17a, respectively.

Scheme VI depicts the final assembly of biphenyl and 4-(1H-pyrrol-1-yl)imidazole fragments. Treatment of any of the 4-(1H-pyrrol-1-yl)imidazoles of structure type 6 with 17 in the presence of a suitable base such as $Na_2CO_3$, $K_2CO_3$, $Cs_2CO_3$, potassium t-butoxide, sodium methoxide, sodium hydride and the like in an inert solvent such as tetrahydrofuran or N,N-dimethylformamide gives rise to protected products such as 18. The regiochemistry of this alkylation process is highly selective for N(1) alkylation due to the steric hinderance to N(3) provided by the adjacent pyrrole ring. The preferred base for the transformation of 6 to 18 is $Cs_2CO_3$ in a solvent of N,N-dimethylformamide effected at ambient temperature. The trityl protecting group of compound 18 is removed by either refluxing with methanol overnight, by heating with methanol and a mild acid catalyst such as aqueous citric acid, or by brief treatment with warm acetic acid to afford 19 which is a compound of Formula I. Compounds of structure 19 where $R^3$ or $R^4$ or both $R^3$ and $R^4$ are esters further deprotection by saponification affords 20 which is also a compound of Formula I. In certain instances it is necessary to account for the reactivity of groups in $R^3$ and $R^4$ as depicted on compounds 18 and 19, adjusting the synthetic strategy slightly in order to obtain additional desired compounds of Formula I. Such adjustments of Scheme VI are within the usual realm of expertise of a practitioner of the art of organic chemistry and include the use of additional protection and deprotection steps and the reordering of synthetic steps. The strategy for assembly of complex organic molecules is described in *The Logic of Chemical Synthesis* by E. J. Corey and Xue-Min Cheng, John Wiley and Sons (1989).

SCHEME I
4-(1H-Pyrrol-1-yl)imidazole Synthesis
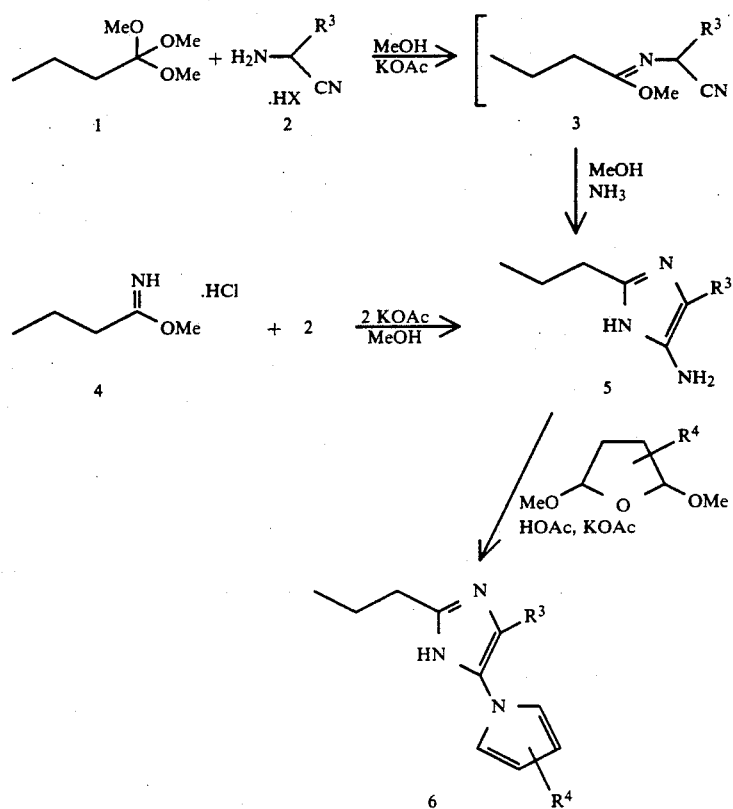
$R^3$ is CN, CO$_2$Et or CO$_2$Me
$R^4$ is H, 2-CH$_3$, 2-CH$_2$CH$_3$, 2,5-(CH$_3$)$_2$, 3-CH$_3$, 3-CH$_2$CH$_3$, 2-CO$_2$Me, 3-CO$_2$Et, 2-CH$_2$CH$_2$CH$_3$-5-CH$_3$ or 2-CH$_3$-3-CO$_2$Me
SCHEME II
Alternative 4-(1H-Pyrrol-1-yl)imidazole Synthesis
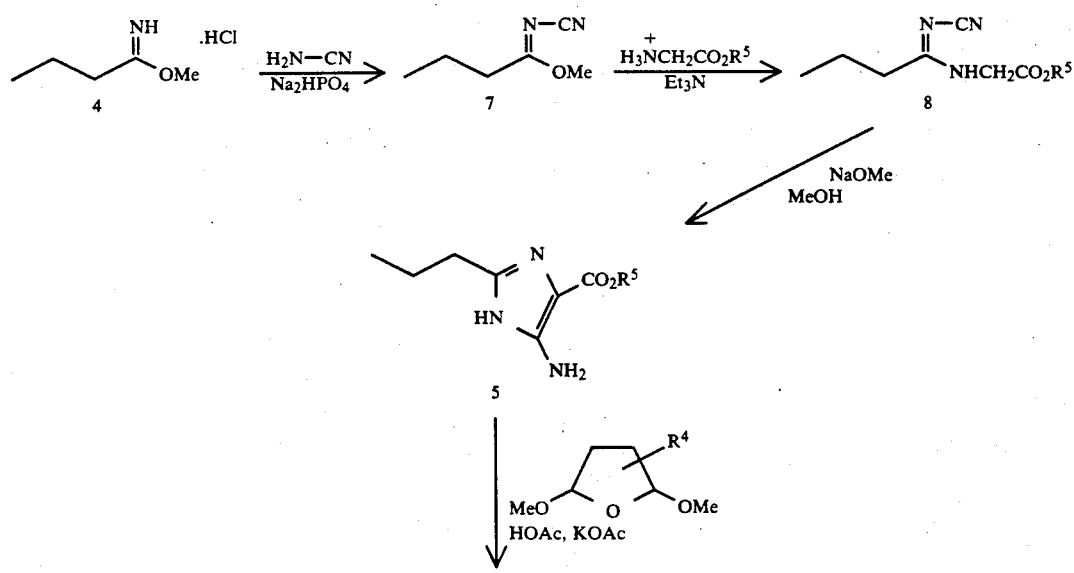

-continued
SCHEME II
Alternative 4-(1H-Pyrrol-1-yl)imidazole Synthesis

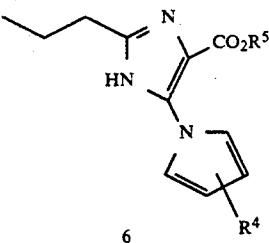

6

$R^5$ is —CH$_3$, —C$_2$H$_5$, —C(CH$_3$)$_3$
$R^4$ is H, 2-CH$_3$, 2-CH$_2$CH$_3$, 2,5-(CH$_3$)$_2$, 3-CH$_3$, 3-CH$_2$CH$_3$,
    2-CO$_2$Me, 3-CO$_2$Et, 2-CH$_2$CH$_2$CH$_3$-5-CH$_3$ or 2-CH$_3$-3-CO$_2$Me

SCHEME III
Transformations of the Imidazole Ring

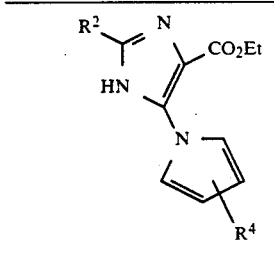

6

↓ LAH
  THF

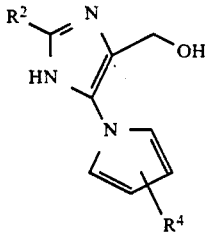

9

↓ MnO$_2$
  THF

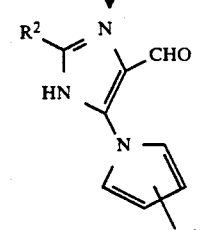

10

CH$_2$(CO$_2$H)$_2$,      (EtO)$_2$POCH$_2$COR$^5$,
piperidine                base

-continued
SCHEME III
Transformations of the Imidazole Ring

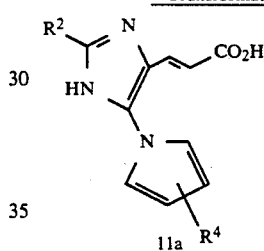  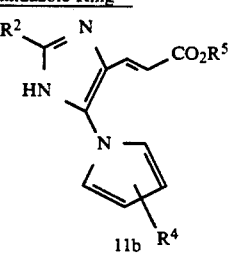

11a     11b

SCHEME IV
Electrophilic Substitution of Pyrrole Ring

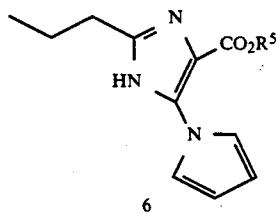

6

E$^+$ {
  HNO$_3$/Ac$_2$O
  2. NCS
  3. ClCOCCl$_3$
  4. NBS
  5. CF$_3$CO$_2$COCF$_3$
}

↓

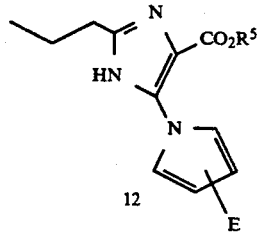

12

E = 2-NO$_2$, 3-NO$_2$, 2-Cl, 2-5(Cl)$_2$,
    2-COCCl$_3$, 2-Br, 2,5(Br)$_2$ or 2-COCF$_3$

SCHEME IVA
Electrophilic Modification of Substituted Pyrroles
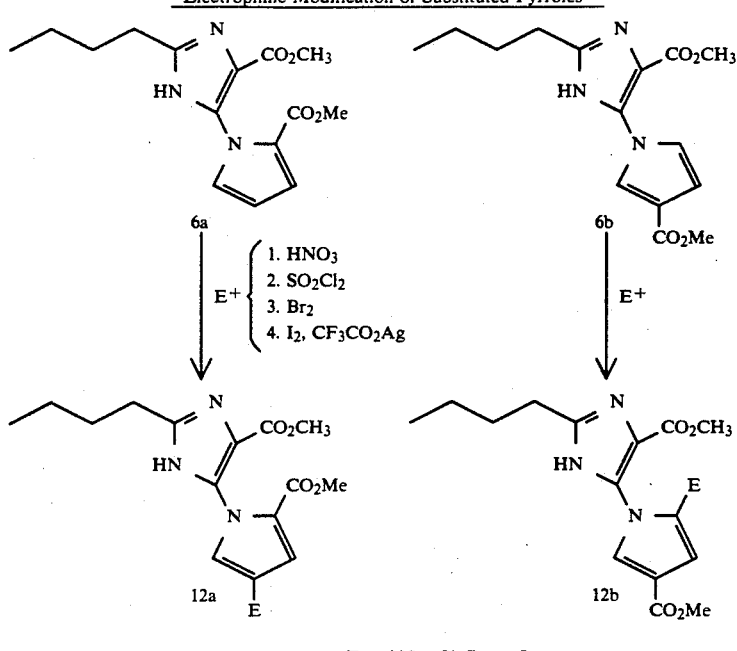
E = $NO_2$, Cl, Br, or I
SCHEME V
Biphenyl Fragment Synthesis
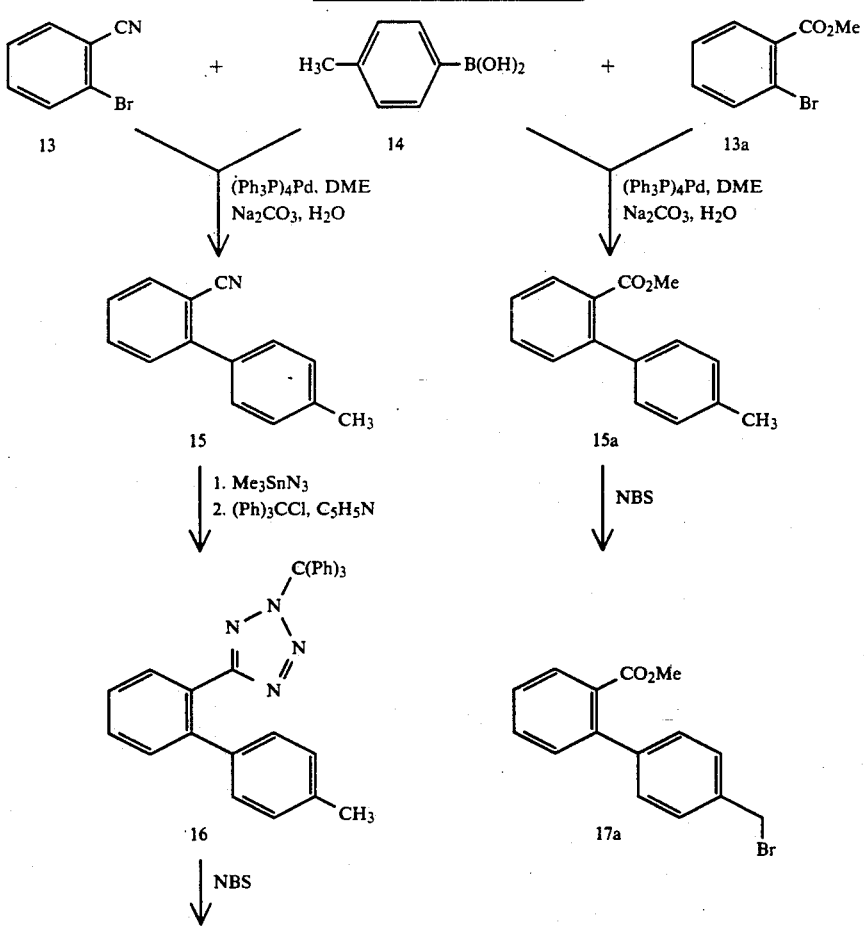

SCHEME V
Biphenyl Fragment Synthesis

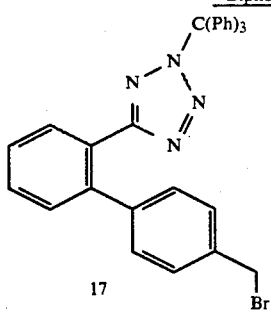

SCHEME VI
Connection of Biphenyl and 4-(1H-Pyrrol-1-yl) imidazole Fragments

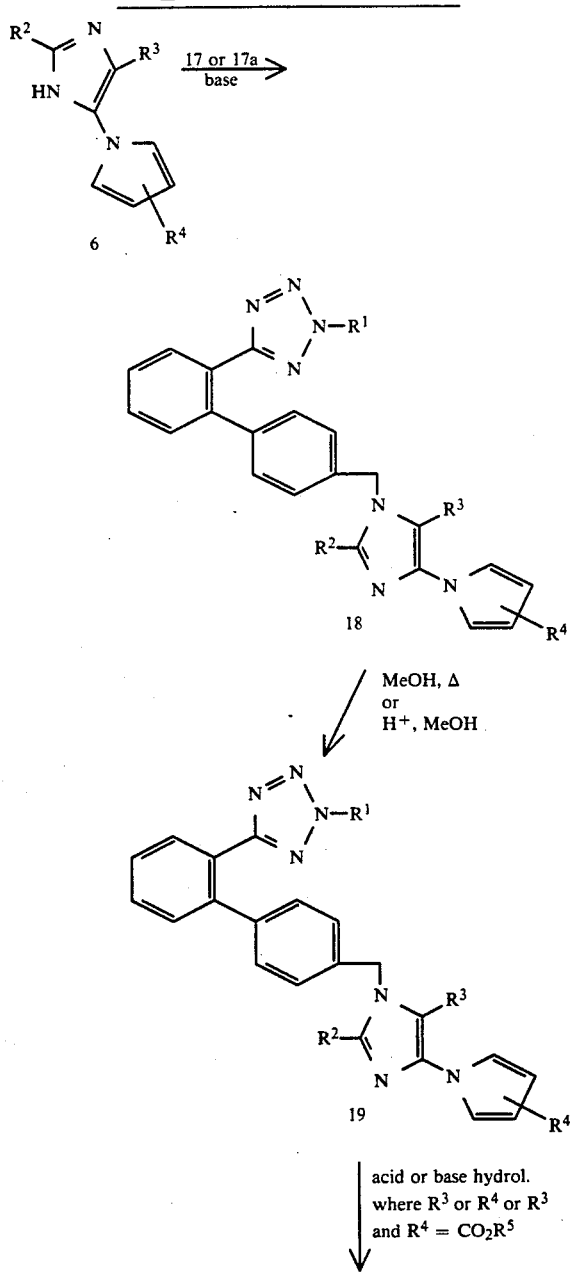

-continued
SCHEME VI
Connection of Biphenyl and 4-(1H-Pyrrol-1-yl) imidazole Fragments

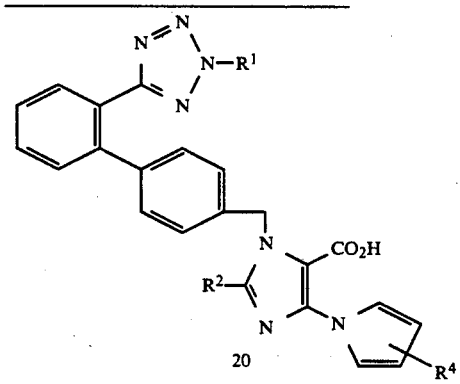

The compounds of Formula I are valuable antagonists of angiotensin II. Dudley, D. T., et al, *Molecular Pharmacology* 38:370–377 (1990) reported the existence of two subclasses of angiotensin II binding sites in rabbit adrenal gland and uterus and in the rat liver which differ in their tissue distribution and affinity for various peptide and nonpeptide ligands. Thus, the compounds of Formula I were tested for their ability to inhibit [$^3$H] angiotensin II binding to rat liver membranes (AT$_1$ test) according to the methods described by Dudley, D. T., et al, *Molecular Pharmacology* 38:370–377 (1990). Compounds of Formula I are active in the AT$_1$ test with IC$_{50}$ values ranging from 0.1 nM to 1.0 μM.

Also, the compounds of Formula I were tested for functional activity in vitro. Thus, the compounds of the present invention were tested for their ability to antagonize angiotensin II induced contractions in rabbit aortic rings according to the method described by Dudley D. T., et al, *Molecular Pharmacology* 38:370–377 (1990). The aforementioned test methods are incorporated herein by reference. Compounds of Formula I are active in this in vitro functional assay with IC$_{50}$ values ranging from 0.1 nM to 1.0 μM.

Finally, the compounds of Formula I were tested in vivo for blood pressure lowering effects in renal hypertensive rats (2 kidney, 1 clip Goldblatt model) according to the method described by S. Sen, et al, in *Hypertension* 1:427–434 (1979) and in *Clin. Soc.* 57:53–62, 1979.

Illustrative of the in vivo antihypertensive activity for compounds of Formula I is the data for 4-[2-(1-oxo-2,2,2-trifluoroethyl)-1H-pyrrol-1-yl]-2propyl-1-[(2'-

(1H-tetrazol-5-yl)biphen-4-yl)methyl]-1H-imidazole-5-carboxylic acid (Example 14). This compound lowers blood pressure by 250 mm Hg and is efficacious for more than 24 hours with a single oral dose of 30 mg/kg in the above rodent model.

The compounds of the present invention can be prepared and administered in a wide variety of oral and parenteral dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxynethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use, the compounds utilized in the pharmaceutical method of this invention are administered at the initial dosage of about 0.1 mg to about 50 mg per kilogram daily. A daily dose range of about 0.5 mg to about 30 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following examples illustrate methods for preparing intermediate and final products of the invention. They are not intended to limit the scope of the invention.

EXAMPLE 1

Methyl propionimidate hydrochloride

Hydrogen chloride gas was bubbled through an ether (500 mL) solution of butyronitrile (275.4 g) and methanol (160 g) for a period of 3 hours. The temperature during the addition rose from 4° to 4° C. and the reaction mixture stirred at −1° C. for 1 hour, then stored at −25° C. for 16 hours. The resulting suspension was stirred at 10° C. and ether (1.8 L) added over a period of 40 minutes. The mixture was stirred for 1 hour at −6° C., then filtered under an atmosphere of N₂. The insoluble product was filtered, washed with ether, and dried to afford 280 g of methyl butyrimidate hydrochloride. The filtrate was cooled to −5° C. for 30 minutes, filtered, and the insoluble product washed with ether to afford an additional 42 g of title product, mp 80°–81° C. MS (DEI) 102 (M+1).

EXAMPLE 2

Methyl N-cyanobutyrimidate

The methyl butyrimidate salt from Example 1 (322 g, 2.34 mol) was dissolved in a 50% aqueous solution of cyanamide (236 g, 2.81 mol) and cooled in an ice bath. Dibasic sodium phosphate (164 g, 1.15 mol) was added to the reaction mixture in portions over a period of 1 hour. The resulting suspension was stirred at room temperature for 2 hours and the liquid decanted from the reaction mixture. The remaining solid was diluted with water (2 L) and extracted with ether (3×600 mL). The combined organic layers were washed with water and dried over anhydrous magnesium sulfate. The solvent was removed under reduced pressure and the residue distilled under high vacuum to afford 258 g of methyl N-cyanobutyrimidate. MS (DEI) 127 (M+1).

EXAMPLE 3

Methyl N-(N'-cyanobutyrimidoyl)glycinate

Methyl N-cyanobutyrimidate (240 g, 1.90 mol) from Example 2 was dissolved in absolute methanol (1.5 L) and glycine methyl ester HCl (250 g, 1.99 mol) added to the reaction mixture. The suspension was cooled to 5° C. and triethylamine (211 g, 2.09 mol) added over a period of 15 minutes. The resulting solution was stirred at 20° C. for 17 hours, then concentrated under reduced pressure to an oily-solid residue (690 g). The residue was taken up in ethyl acetate and the insoluble salts removed by filtration. The filtrate was washed with water followed by 10% aqueous sodium chloride solution. The organic layer was dried over anhydrous magnesium sulfate and evaporated to dryness under reduced pressure. This product (370 g) was used in the next step without further purification.

EXAMPLE 4

Methyl 4-amino-2-propylimidazole-5-carboxylate

To stirred methanol at −2° C. was added sodium methoxide (108 g, 2.0 mol) in portions over a period of 40 minutes. To this clear solution at −3° C. was added a solution of methyl N-(N'-cyanobutyrimidoyl)glycinate (Example 3, 344 g, 1.9 mol) in methanol (600 mL) over a period of 30 minutes. The resulting orange solution was allowed to warm to 13° C. over a period of 1 hour, then refluxed for 1 hour. The dark solution was cooled to room temperature and evaporated to dryness under reduced pressure. The residue was partitioned between water and ethyl acetate. The aqueous layer was extracted with ethyl acetate (4×1 L) and the combined organic layers washed with a saturated aqueous solution of sodium chloride. The combined organic layers were dried over anhydrous magnesium sulfate, filtered, and the filtrate evaporated to dryness under reduced pressure. The residue was recrystallized from ethyl acetate at −10° C. to afford 131 g (38% yield) of methyl 4-amino-2-propylimidazol-5-carboxylate, mp 133°–136° C. MS (DEI) 184 (M+1).

EXAMPLE 5

Methyl 2-propyl-4-(1H-pyrrol-1-yl)imidazole-5-carboxylate

To stirred acetic acid (1.5 L) at 80° C. was added over a 5-minute period a mixture of methyl 4-amino-2-propylimidazol-5-carboxylate (Example 4, 145 g, 0.798 mol) and sodium acetate (388 g, 4.73 mol). The mixture was heated at reflux for 5 minutes and then 2,5-dimethoxy-tetrahydrofuran (117 g, 0.885 mol) added all at once. The resulting dark solution was refluxed for 20 minutes, then poured onto ice. The gummy mixture was extracted with dichloromethane, the combined organic layers washed with water and dried over anhydrous magnesium sulfate. The filtrate was concentrated under reduced pressure and the residue dissolved in dichloromethane (2 L). The dichloromethane solution was treated with silica gel (500 g) and the suspension filtered through a bed of silica gel (300 g) eluting with dichloromethane. The filtrate was evaporated to dryness under reduced pressure and the crude product recrystallized from ether/hexane (2:1) to provide 86 g (46% yield) methyl 2-propyl-4-(1H-pyrrol-1-yl)imidazol-5-carboxylate, mp 135°–138° C. MS (DEI) 234 (M+1).

EXAMPLE 6

Methyl 2-propyl-4-[2-(1-oxo-2,2,2-trifluoroethyl)-1H-pyrrol-1-yl]imidazol-5-carboxylate To a stirred solution of the methyl 2-propyl-4-(1H-pyrrol-1-yl)imidazol-5-carboxylate (Example 5, 26 g, 0.11 mol) in dichloromethane (500 mL) at room temperature was added trifluoroacetic anhydride (46.61 mL, 0.33 mol) in one portion. The resulting solution was stirred at room temperature for 18 hours, then cooled to 5° C. in an ice bath. A saturated aqueous solution of sodium bicarbonate (100 mL) was added slowly and the mixture stirred for 10 minutes. The organic layer was separated, washed with a saturated aqueous solution of sodium bicarbonate, then dried over anhydrous magnesium sulfate. The solvent was evaporated to dryness under reduced pressure and the residue taken-up in ether. The crystallizing mixture was cooled to −10° C. and the product collected by filtration to provide 23 g (62% yield) of the title compound, mp 158°–159° C.; MS (DEI) 329 (M+).

EXAMPLE 7

4-Amino-2-butyl-5-cyanoimidazole

A solution of potassium acetate (2.94 g), anhydrous methanol (30 mL) and trimethyl orthovalerate (9.73 g) was treated with solid aminomalononitrile p-toluenesulfonate and the resulting suspension was stirred at room temperature for 18 hours under nitrogen atmosphere. Solids were removed by filtration and rinsed with anhydrous methanol (30 mL). The combined filtrate and washings were evaporated and the residue was treated with saturated, anhydrous methanolic ammonia (100 mL) at room temperature. The resulting solution was stirred for 18 hours then it was concentrated to about 50 mL. The concentrate was treated with activated charcoal and filtered. The filtrate was evaporated and the residue was purified by flash chromatography on silica gel, eluting with ethyl acetate-hexane (70:30) to give pure product as a gum upon evaporation. This gum was redissolved in chloroform ether (1:2) and concentrated at reduced pressure to afford a solid which was collected by filtration and rinsed with ether affording the desired product, mp 115°–116° C. $^1$H-NMR (CDCl$_3$) δ 9.0 (br, 1H), 4.2 (br, 2H), 2.6 (t, 2H), 1.6 (m, 2H), 1.3 (m, 2H), 0.9 (t, 3H).

EXAMPLE 8

2-Butyl-5-cyano-4-(1H-pyrrol-1-yl)imidazole

A solution of potassium acetate (5.0 g), acetic acid (22 mL) and 4-amino-2-butyl-5-cyanoimidazole (Example 7, 1.45 g) was heated to reflux and treated with 2,5-dimethoxy-tetrahydrofuran (1.25 mL). The reaction was held at reflux for 1 minute then cooled back to room temperature with an ice bath. The majority of the acetic acid was evaporated at reduced pressure then the residue was partitioned between ethyl acetate and 10% aqueous K$_2$CO$_3$ (120 mL) each. The organic layer was dried over MgSO$_4$ and evaporated. The residue was purified by flash chromatography on silica gel, eluting with hexane-ethyl acetate (90:10 to 80:20). Evaporation of solvents gave a gum that was redissolved in dichloromethane and evaporated once again. The residual oil was held under a vacuum overnight to afford a waxy solid. $^1$H-NMR (CDCl$_3$) δ 9.9 (br, 1H), 7.4 (s, 2H), 6.3 (s, 2H), 2.7 (t, 2H), 1.7 (m, 2H), 1.4 (m, 2H), 1.0 (t, 3H).

EXAMPLE 9

2-Cyano 4'-methylbiphenyl

Nitrogen was bubbled through a solution of 2-bromobenzonitrile (309.4 g, 1.70 mol) in dimethoxyethane (4.2 L) for 30 minutes then the following reagents added in succession: tetrakis(triphenylphosphine)palladium(O), (95 g, 0.082 mol); 2M aqueous sodium carbonate solution (1785 mL, 3.57 mol); and p-tolylboronic acid (239.1 g, 1.76 mol). The reaction mixture was heated under an atmosphere of nitrogen at 70° to 78° C. for 19 hours. The two-phase mixture was cooled to room temperature and the layers separated. The organic layer was evaporated to dryness under reduced pressure. The aqueous layer was extracted with ether (3×1.2 L) and the extracts added to the organic residue. The insoluble material was filtered off and washed with ether. The filtrate was dried over anhydrous magnesium sulfate and evaporated to dryness under reduced pressure. The oily residue was filtered to remove the solids and the filtrate distilled under high vacuum (0.1–0.2 torr) collecting the fraction boiling between 135° to 140° C. to afford 325 g of 2-cyano-4'-methylbiphenyl. MS (DEI) 193 (M+).

EXAMPLE 10

N-Trimethylstannyl-5-(4'-methylbiphenyl-2-yl)tetrazole

A solution of 2-cyano-4'-methylbiphenyl (1.93 g) in toluene (25 mL) was treated with trimethyltin azide (2.65 g) and heated at reflux for 24 hours. The resulting suspension was cooled to 70° C. and filtered. The collected solid was dried at reduced pressure to give the title compound. $^1$H-NMR (CDCl$_3$) δ 7.5 (m, 4H), 7.0 (q, 4H), 2.3 (s, 3H), 0.4 (s, 9H).

EXAMPLE 11

N-Triphenylmethyl-5-(4'-methylbiphenyl-2-yl)tetrazole

A mixture of N-trimethylstannyl 5 (4'-methylbiphenyl-2-yl)tetrazole (Example 10, 0.4 g) and anhydrous pyridine (10 mL) was treated with triphenylmethyl chloride (0.3 g) and stirred at room temperature under a nitrogen atmosphere for 48 hours. The resulting solution was evaporated and the residue was partitioned between dichloromethane and saturated aqueous CuSO$_4$. The organic layer was dried over MgSO$_4$ and evaporated. The residual solid was triturated with diisopropyl ether and collected by filtration to give the title compound, mp 163°–165° C. (decomp., gas evol.).

EXAMPLE 12

N-Triphenylmethyl-5-(4'-(bromomethyl)biphenyl-2-yl]tetrazole

A mixture of N-triphenylmethyl 5-(4'-methylbiphenyl-2-yl)tetrazole (Example 11, 12.7 g), N-bromosuccinimide (4.6 g), carbon tetrachloride (300 mL), and benzoyl peroxide (75 mg) was heated at reflux for 2.5 hours. The cooled suspension was filtered and the filtrate was evaporated to give the title compound as a crystalline solid. $^1$H-NMR (CDCl$_3$) δ 8.2 6.7 (complex, 23H), 4.3 (s, 2H).

EXAMPLE 13

Methyl 4-[2-(1-oxo-2,2,2-trifluoroethyl)-1H-pyrrol-1-yl]-2-propyl-1-[(2'-(1H-tetrazol-5-yl)biphen-4-yl)methyl]1H-imidazole-5-carboxylate Methyl 2-propyl-4-[2-(1-oxo-2,2,2-trifluoroethyl)-1H-pyrrol-1-yl]imidazole-5-carboxylate (15 g, 0.046 mol) from Example 6 was dissolved in DMF (500 mL) and Cs$_2$CO$_3$ (32.9 g, 0.1 mol) added. After 5 minutes, N-triphenylmethyl-5-[4, (bromomethyl)-biphenyl-2-yl]tetrazole (Example 12, 26.9 g, 0.048 mol) was added and the reaction mixture stirred at room temperature for 6 hours. The reaction was filtered to remove insoluble salts and the DMF removed high vacuum. The residue was partitioned between ethyl acetate (150 mL) and water (50 mL). The organic layer was extracted with brine, dried over anhydrous magnesium sulfate, and the solvent evaporated under reduced pressure. Chromatography of the residue on silica gel, eluting with a gradient of ethyl acetate/hexane (1:4) to ethyl acetate/hexane (1:1) afforded 25 g of the title compound in its triphenylmethyl-protected form. The triphenylmethyl protecting group was removed by refluxing in methanol (280 mL) containing 10% aqueous citric acid (28 mL) for 4 hours. The reaction mixture was diluted with water (100 mL) and the milky solution extracted with several times with hexane The aqueous layer was extracted with ethyl acetate and the combined organic layers extracted with brine. The organic layer was dried over anhydrous magnesium sulfate and the solvent removed under reduced pressure. The residue was recrystallized using Hexane/ethyl acetate(1:1) to afford 13.4 g of the title compound. MS (FAB, thioglycerol) 564(M+1), mp 135°–137° C.

EXAMPLE 14

4-[2-(1-Oxo-2,2,2-trifluoroethyl)-1H-pyrrol 1-yl]-2-propyl-1-[(2'-(1H-tetrazol-5-yl)biphen-4-yl)methyl]-1H-imidazole-5-carboxylic acid 4-[2-(1-Oxo-2,2,2-trifluoroethyl)-1H-pyrrol-1-yl]-2-propyl-1-[(2'-(1H-tetrazol-5-yl)biphen-4-yl)methyl]-1H-imidazole-5-carboxylate (2.5 g) from Example 13 was dissolved in DMF (45 mL). Water (0.4 mL) followed by potassium carbonate (3.1 g) were added and the reaction mixture stirred at room temperature for 48 hours. Tlc of the reaction mixture showed the reaction to be incomplete. Additional potassium carbonate (0.6 g) and water (0.2 mL) were added and the reaction mixture stirred at room temperature for an another 18 hours. The insoluble materials were removed from the reaction mixture by filtration and washed with DMF A 10% citric acid solution (100 mL) was added slowly to the filtrate and the resulting mixture extracted with ethyl acetate. The organic layer was washed with brine, dried over anhydrous magnesium sulfate, and the solvent removed under reduced pressure. The residue was recrystallized from hexane/ethyl acetate to afford 2.06 g (85% yield) of the title compound, mp 185°–188° C., MS (FAB, thioglycerol) 550.3 (M+1).

EXAMPLE 15

2-Butyl-5-cyano-4-(1H-pyrrol-1-yl)-1-(2'-(1H-tetrazol-5-yl)biphen-4-yl)methyl]-1H-imidazole A solution of 2-butyl-5-cyano-4-(1H-pyrrol-1-yl)imidazole (Example 8, 1.7 g) in anhydrous tetrahydrofuran (20 mL) was treated with a solution of potassium tert-butoxide (0.97 g) in anhydrous tetrahydrofuran (20 mL) at room temperature. The mixture was stirred for 5 minutes then a solution of N-triphenylmethyl-5-[4'-(bromomethyl)biphenyl-2-yl]tetrazole (Example 12, 6.0 g) in anhydrous tetrahydrofuran (20 mL) was added. The reaction was stirred at room temperature under nitrogen atmosphere for 18 hours. The resulting suspension was filtered and the filtrate was evaporated. The residue was purified by flash chromatography on silica gel, eluting with chloroform-hexane (90:10) to give the title compound in its triphenylmethyl-protected form. The triphenylmethyl protecting group was removed by refluxing in methanol for 24 hours. Evaporation gave a residue that was purified by chromatography on silica gel, eluting with a gradient of ethyl acetate-hexane (50:50) to ethyl acetate. Evaporation of solvents gave a gum that was redissolved in dichloromethane and evaporated to give the title compound as a solid foam. MS (FAB, thioglycerol) 470 (m+Na-1), 448 (m).

EXAMPLE 16

2-Butyl-4-(1H-pyrrol-1-yl)-1-[(2'-(1H-tetrazol-5-yl)biphen-4-yl)methyl]-1H-imidazole-5-carboxylic acid A mixture of 2-butyl-5-cyano-4-(1H-pyrrol-1-yl)-1-[(2'-(1H-tetrazol-5-yl)biphen-4-yl)methyl]-1H-imidazole (Example 15, 1.4 g) and 2N NaOH (75 mL) was heated at reflux for 24 hours. The cooled solution was acidified to pH 3.5 by portionwise addition of citric acid. The resulting precipitate was collected by filtration and rinsed well with water. The solid was then purified by $C_{18}$-reversed phase chromatography eluting with acetonitrile water (40:60). The majority of the acetonitrile was evaporated from the pure fractions at reduced pressure, keeping the temperature below 30° C. The remaining aqueous portion was washed with ethyl acetate and the organic layer was dried over anhydrous magnesium sulfate and evaporated. The residue was dissolved in ether and evaporated once again to give the title compound as a colorless powder. MS (FAB, thioglycerol) 468 (m+1), 424 (m-$CO_2$+1).

EXAMPLE 17

2-Butyl-4-(1H-pyrrol-1-yl)-1-[(2'-(1H-tetrazol-5-yl)biphen-4-yl)methyl]-1H-imidazole A suspension of 2-butyl-4-(1H-pyrrol-1-yl)-1-[(2'-(1H-tetrazol-5-yl)biphen-4-yl)methyl]-1H-imidazole-5-carboxylic acid (Example 16, 50 mg) in toluene (10 mL) was heated at reflux for 1 hour. Evaporation gave a gummy solid that was redissolved in ether and evaporated again to give the title compound as a colorless powder. $^1$H-NMR (CDCl$_3$) δ 7.9 (d, 1H), 7.6 (m, 2H), 7.4 (d, 2H), 7.1 (d, 2H), 6.9 (d, 2H), 6.8 (s, 2H), 6.5 (s, 1H), 6.1 (s, 2H), 5.0 (s, 2H), 2.4 (t, 2H), 1.6 (m, 2H), 1.3 (m, 2H), 0.9 (t, 3H).

EXAMPLE 18

4-Amino-5-cyano-2-propylimidazole

Using the method of Example 7, trimethyl orthobutyrate was substituted for trimethyl orthovalerate to afford the title compound. Recrystallization from tert-butyl methyl ether gave analytically pure material, mp 117°-119° C. $^1$H-NMR (DMSO-d$_6$) δ 5.9 (br, 2H), 5.7 (br, 1H), 2.4 (m, 2H), 1.6 (m, 2H), 0.9 (t, 3H).

EXAMPLE 19

5-Cyano-2-propyl-4-(1H-pyrrol-1-yl)imidazole

4-Amino-5-cyano-2-propylimidazole (Example 18) was treated as in Example 8 to afford the title compound as a crystalline solid upon evaporation of chromatography solvents, mp 75°-78° C. $^1$H-NMR (CDCl$_3$) δ 10.1 (br, 1H), 7.4 (s, 2H), 6.4 (s, 2H), 2.7 (t, 2H), 1.8 (m, 2H), 1.0 (t, 3H).

EXAMPLE 20

Ethyl 4-amino-2-butylimidazole-5-carboxylate

A mixture of methyl iminovalerate hydrochloride (4.8 g), ethyl 2-amino-2-cyanoacetate oxalate (4.0 g), anhydrous sodium acetate (9.1 g) and absolute ethanol (75 mL) was stirred at room temperature for 18 hours. Solids were removed by filtration and the filtrate was evaporated. The residue was partitioned between ethyl acetate and water. The ethyl acetate layer was washed with saturated NaCl, dried over MgSO$_4$, and evaporated Flash chromatography on silica gel, eluting with a gradient of dichloromethane-ethyl acetate (75:25) to ethyl acetate gives the title compound (2.7 g) as a pale yellow solid, mp 103°-106° C. MS (DEI) 211 (m).

EXAMPLE 21

Ethyl 2-Butyl-4-(1H-pyrrol-1-yl)imidazole-5-carboxylate

Ethyl 4-amino-2-butylimidazole-5-carboxylate (Example 20) was treated as in Example 8 to provide the title compound. Purification was achieved by flash chromatography on silica gel, eluting with dichloromethane-ethyl acetate (90:10), mp 74°-77° C. MS (CI, CH$_4$) 262 (m+1).

EXAMPLE 22

Cyano 2-propyl-4-(1H-pyrrol-1-yl)-1-[(2'-(1H-tetrazol-5-yl)biphen-4-yl)methyl]-1H-imidazole Using the method described in Example 15, 5-cyano 2 propyl-4-(1H-pyrrol-1-yl)imidazole (Example 19, 2.0 g), potassium tert butoxide (1.2 g) and N-triphenylmethyl-5-[4'-(bromomethyl)biphenyl-2yl]tetrazole (Example 12, 7.0 g) were reacted to give the title product in its triphenylmethyl protected form after purification by chromatography. This material was dissolved in methanol (200 mL), treated with aqueous 10% citric acid (10 mL) and heated at reflux for 2.5 hours. The resulting solution was diluted with water (40 mL) and washed twice with hexanes. The methanol-water layer was evaporated and the residue was partitioned between ethyl acetate and water. The organic layer was dried over anhydrous magnesium sulfate and evaporated to a gum. This gum was dissolved in tert-butyl methyl ether and evaporated to a gum which was allowed to stand until seed crystals formed. Trituration with tert-butyl methyl ether gives the title compound as a crystalline solid, mp 179°-181° C. MS (CI, CH$_4$+NH$_3$) 435 (m+1).

EXAMPLE 23

Ethyl 2-butyl-4-(1H-pyrrol-1-yl)-1-[(2′-(1H-tetrazol-5-yl)biphen-4-yl)methyl]-1H-imidazole-5-carboxylate Using the method described in Example 15, ethyl 2-butyl-4-(1H-pyrrol-1-yl)imidazole-5-carboxylate (Example 21) and N-triphenylmethyl-5-[4′-(bromomethyl)-biphenyl-2-yl]tetrazole (Example 12) are reacted and deprotected to give the title compound.

EXAMPLE 24

2-Propyl-4-(1H-pyrrol-1-yl)-1-[(2′-(1H-tetrazol-5-yl)biphen-4-yl)methyl]-1H-imidazole-5-carboxylic acid 5-Cyano-2-propyl 4-(1H-pyrrol-1-yl) 1-[(2′-(1H-tetrazol-5-yl)biphen-4-yl)methyl]-1H-imidazole (Example 22, 2.2 g) was treated with 2N KOH (75 mL) and heated at reflux for 12 hours. The resulting solution was cooled on an ice bath and treated dropwise with concentrated aqueous HCl (8 mL) followed by dropwise addition of aqueous 10% citric acid (50 mL). The resulting precipitate was collected by filtration and then it was partitioned between ethyl acetate and 10% citric acid. The organic layer was washed with brine, dried over anhydrous magnesium sulfate and concentrated on a rotary evaporator, keeping the temperature below 25° C. to give a foam. This foam was dissolved in ether-$CH_2Cl_2$ (1:1) and diluted to turbidity with hexanes. Evaporation of solvents as above gives the title compound as a colorless powder MS (FAB, thioglycerol) 454 (m+1), 410 (m-$CO_2$+1).

EXAMPLE 25

2-Propyl-4-(1H-pyrrol-1-yl)-1-[(2′-(1H-tetrazol-5-yl)biphen-4-yl)methyl]-1H-imidazole Using the method described in Example 17, 2-propyl-4-(1H-pyrrol-1-yl)-1-[(2′-(1H-tetrazol-5-yl)biphenyl)-methyl]imidazole-5-carboxylic acid (Example 24) is decarboxylated to give the title compound.

EXAMPLE 26

5-Cyano-4-[2-(1-oxo-2,2,2-trifluoroethyl)-1H-pyrrol-1-yl]-2-propylimidazole

A solution of the 5-cyano-2-propyl-4-(1H-pyrrol-1-yl)imidazole (Example 19, 2.2 g) in toluene (65 mL) was treated with trifluoroacetic anhydride (4.8 mL) and heated at reflux for 2 hours After cooling to room temperature, the resulting solution was diluted with ethyl acetate (100 mL) and stirred vigorously with 10% $K_2CO_3$ (100 mL) for 15 minutes. The organic layer was separated, dried over anhydrous magnesium sulfate and evaporated. The residual gum was purified by flash chromatography on silica gel, eluting with hexane ethyl acetate (70:30) to afford an oil upon evaporation of solvents. This oil was dissolved in ether, and diluted gradually with hexanes to induce crystallization, affording the title compound as a colorless solid, mp 104°–105° C. $^1$H-NMR ($CDCl_3$) δ 7.3 (m, 2H), 6.5 (t, 1H), 2.6 (t, 2H), 1.7 (m, 2H), 0.9 (t, 3H). IR ($CDCl_3$) $cm^{-1}$ 2240 (CN), 1685 (CO).

EXAMPLE 27

5-Cyano-4-[2-(1-oxo-2,2,2-trifluoroethyl)-1H-pyrrol-1-yl]-2-propyl-1-[(2′-(1H-tetrazol-5-yl)biphen-4-yl)methyl]-1H-imidazole N-triphenylmethyl 5-[4′-(bromomethyl)biphenyl-2yl]tetrazole (Example 26, 2.1 g), 5-cyano-4-[2-(1-oxo-2,2,2-trifluoroethyl)-1H-pyrrol-1-yl]-2-propylimidazole (Example 26, 0.89 g), N,N-dimethylformamide (10 mL), and anhydrous $K_2CO_3$ (0.5 g) were stirred at room temperature under nitrogen atmosphere for 24 hours. Ethyl acetate (50 mL) was added and inorganic solids were removed by filtration. The filtrate was evaporated at reduced pressure and the major product was isolated by flash chromatography on silica gel (toluene-acetonitrile 96:4) to afford the title compound in its triphenylmethyl protected form (1.3 g). This material was dissolved in methanol (50 mL), treated with aqueous 10% citric acid (1.5 mL) and heated at reflux for 90 minutes. After cooling to room temperature, water (10 mL) and hexanes (100 mL) were added and the mixture was shaken vigorously. The methanol layer was separated, washed again with hexanes and evaporated. The residue was partitioned between ethyl acetate and water. The ethyl acetate layer was dried over anhydrous magnesium sulfate and evaporated. The resulting gum was dissolved in ether, concentrated and allowed to stand overnight to give some seed crystals. The remaining gum was dissolved in tertbutyl methyl ether, seeded and diluted with diisopropyl ether. Crystallization gave the title product after filtration. MS (CI, $CH_4+NH_3$) 531 (m+1).

EXAMPLE 28

5-Cyano-4-[2-(1-hydroxy-2,2,2-trifluoroethyl)-1H-pyrrol-1-yl]-2-propyl-1-[(2′-(1H-tetrazol-5-yl)biphen-4-yl)methyl]-1H-imidazole A solution of 5-cyano-4-[2-(1-oxo-2,2,2-trifluoroethyl)-1H-pyrrol-1-yl]-2 propyl-1-[(2′-(1H-tetrazol-5-yl)biphen-4-yl)methyl]-1H-imidazole (Example 27, 300 mg) in ethanol (5 mL) was chilled to 10° C. and treated with $NaBH_4$ (30 mg). There was a period of rapid gas evolution then the reaction was stirred for 1 hour. Acetone (0.1 mL) was added and the reaction was stirred 10 minutes longer before partitioning between ethyl acetate and 10% citric acid (aq). The organic layer was washed with saturated aqueous NaCl, dried over $MgSO_4$ and evaporated. Flash chromatography on silica gel, eluting with $CHCl_3$ $CH_3OH$—$CH_3CN$ (90:5:5) gives the title compound as a foam upon evaporation of solvents. The foam was triturated with hexane diisopropyl ether (3:1) to give a colorless powder. MS (FAB, thioglycerol) 533 (m+1).

EXAMPLE 29

2-Butyl-5-(hydroxymethyl)-4-(1H-pyrrol-1-yl)imidazole

A solution of ethyl 2-butyl-4-(1H-pyrrol-1-yl)imidazol-5-carboxylate (Example 21, 0.5 g) in tetrahydrofuran (15 mL) was treated with a 1M solution of $LiAlH_4$ in ether (2.1 mL). The reaction was stirred overnight at room temperature then quenched by addition of saturated aqueous $(NH_4)_2SO_4$. The resulting suspension was extracted three times with ethyl acetate and the combined organic layers were dried over anhydrous magnesium sulfate and evaporated to afford the title compound as an off-white solid MS (DEI) 205 (m)

EXAMPLE 30

5-Cyano-4-(2,5-dichloro-1H-pyrrol-1-yl)-2-propylimidazole

A mixture of 5-cyano-2-propyl-4-(1H-pyrrol-1-yl)imidazole (Example 19, 200 mg), N-chlorosuccinimide (270 mg) and tetrahydrofuran (4 mL) was stirred at room temperature for 24 hours. Evaporation of solvents, followed by flash chromatography on silica gel (hexane-ethyl acetate, 70:30) gives the title product. $^1$H-NMR (CDCl$_3$) δ 6.1 (s, 2H), 2.7 (t, 2H), 1.8 (m, 2H), 0.9 (t, 3H).

EXAMPLE 31

1-[5-Carboxy-2-propyl-1-[(2′-(1H-tetrazol-5-yl)biphen-4-yl)methyl]-1H-imidazol-4-yl]-1H-pyrrol-2-carboxylic acid Methyl 4-[2-(1-oxo-2,2,2-trifluoroethyl)-1H-pyrrol-1-yl]-2-propyl-1-[(2′-(1H-tetrazol-5-yl)biphen-4-yl)methyl]-1H-imidazole-5-carboxylate (Example 13, 0.8 g) was dissolved in a solution sodium hydroxide (1.68 g) in water (14 mL) and the resulting solution refluxed overnight. After cooling in an ice bath, conc HCl was added dropwise until the pH of the mixture was between 3-4. The insoluble product was collected by filtration, washed several times with water, and dried under reduced pressure overnight at room temperature to afford 0.85 g of the title compound $^1$H-NMR (DMSO-d$_6$) δ 7.8 7.5 (m, 4H), 7.3-7.0 (m, 5H), 6.9 (m, H), 6.3 (m, 1H), 5.7 (s, 2H), 2.6 (t, 2H), 1.7 1.4 (m, 2H), 0.9 (t, 3H).

EXAMPLE 32

2-Butyl-5-(hydroxymethyl)-4-(1H-pyrrol-1-yl)-1-[(2′-(1H-tetrazol-5-yl)biphen-4-yl)methyl]-1H-imidazole Using the method described in Example 13, 2-butyl-5-(hydroxymethyl)-4-(1H-pyrrol-1-yl)imidazole-5-carboxylate (Example 29) and N-triphenylmethyl-5-[4′-(bromomethyl)biphenyl-2-yl]tetrazole (Example 12) are reacted and deprotected to give the title compound.

EXAMPLE 33

5-Cyano-4-(2,5-dichloro-1H-pyrrol-1-yl)-2-propyl-1-[(2′-(1H-tetrazol-5-yl)biphen-4-yl)methyl]-1H-imidazole Using the procedure from Example 13, 5-cyano-4-(2,5-dichloro-1H-pyrrol-1-yl)-2-propylimidazole (Example 30) and N-triphenylethyl-5-[4′-(bromomethyl)-bipheyl-2-yl]tetrazole (Example 12) are reacted and deprotected to give the title compound.

EXAMPLE 34

Methyl 1-(5-cyano-2-propylimidazol-4-yl)-1H-pyrrole-2-carboxylate

Using the method of Example 5, 4-amino-5-cyano-2-propylimidazole (Example 7) was reacted with methyl 2,5-dimethoxy-tetrahydrofuran-2-carboxylate to afford the title compound. $^1$H-NMR 9.4 (br, 2H), 7.3 (m, 1H), 7.2 (m, 1 H), 6.4 (t, 1H), 3.8 (s, 3H), 2.7 (t, 2H), 1.8 (m, 2H), 1.0 (t, 3H).

EXAMPLE 35

Methyl 1-[5-cyano-2-propyl-1-[(2′-(1H-tetrazol-5-yl)biphen-4-yl)methyl]-1H-imidazol-4-yl]-1H-pyrrole-2-carboxylate Using the procedure from Example 13, methyl 1-(5-cyano-2-propylimidazol-4-yl)-1H-pyrrole-2-carboxylate (Example 34) and N-triphenylmethyl-5-[4′-(bromomethyl)biphenyl-2-yl]tetrazole (Example 12) were reacted and deprotected to give the title compound MS (CI, CH$_4$+NH$_3$) 507(M+CH$_3$).

EXAMPLE 36

1-[5-Cyano-2-propyl-1-[(2′-(1H-tetrazol-5-yl)biphen-4-yl)methyl]-1H-imidazol-4-yl]-1H-pyrrole-2-carboxylic acid A solution of methyl 1-[5-cyano-2-propyl-1-[(2′-(1H-tetrazol-5-yl)biphen-4-yl)methyl]-1H-imidazol-4-yl]1H-pyrrole-2-carboxylate (Example 35) in tetrahydrofuran-methanol (2:1) was treated with two equivalents of 1N NaOH at 0° C. The reaction mixture was stirred at reflux for 20 hours then treated with two equivalents of 1N HCl. The reaction mixture was then partitioned between ethyl acetate and brine and the organic layer is dried over MgSO$_4$ and evaporated to afford the title compound. MS (FAB, thioglycerol) 479 (M+1).

EXAMPLE 37

Methyl cylcopropylformimidate hydrochloride

Using an analogous procedure to that described in Example 1, but starting from cyclopropyl cyanide was obtained the title compound methyl cyclopropylimidate hydrochloride. $^1$H-NMR (CDCl$_3$) 12.42 (br s, 1H), 11.28 (br. s, 1H), 4.21 (s, 3H), 2.42 (m, 1H), 1.23 (m, 4H).

EXAMPLE 38

Methyl N-cyanocyclopropylforimidate

Using an analogous procedure to that described in Example 2, but starting from methyl cyclopropylfornimidate hydrochloride (Example 37) afforded the title compound methyl N cyano cyclopropylformimidate. $^1$H-NMR (CDCl$_3$) 3.80 (s, 3H), 2.27 (m, 1H), 1.19 (m, 4H).

EXAMPLE 39

Methyl N-(N′-cyano-cylcopropylfornimidoyl)glycinate

Using an analogous procedure to that described in Example 3, but starting from methyl N-cyano cyclopropylformimidate (Example 38) was obtained the title compound methyl N-(N′-cyanocyclopropyl formimidoyl)glycinate. $^1$H-NMR (CDCl$_3$) 6.10 (br s, 1H), 4.04 (d, 2H), 3.79 (s, 3H), 2.18 (m, 1H), 1.12 (m, 4H).

EXAMPLE 40

Methyl 4-amino-2-cyclopropylimidazole-5-carboxylate

Using an analogous procedure to that described in Example 4, but starting from methyl N-(N′-cyanocylcopropylformimidoyl)glycinate (Example 39) was obtained the title compound methyl 4-amino-2-cyclopropylimidazole 5-carboxylate in 78% yield. MS (DEI) 181(M+) and 182(M+1).

EXAMPLE 41

Methyl 2-cyclopropyl-4-(2,5-dimethyl-1H-pyrrol-1-yl)imidazole-5-carboxylate

A suspension of methyl 4-amino-2-cyclopropylimidazole-5-carboxylate (Example 40, 5.72 g, 0.032 mol) in ethanol (40 mL) was treated with acetic acid (25 mL) and the mixture refluxed to effect solution. To the hot solution was added acetonylacetone (5.41 g, 0.047 mol) and the whole stirred and refluxed for 18 hours. The solvent was removed under reduced pressure and the residue purified by flash chromatography eluting with a gradient of $CH_2Cl_2$ to 20% EtOAc in $CH_2Cl_2$ to afford 7.93 g of the title compound methyl 2-cyclopropyl-4-(2,5-dimethyl-1H-pyrrol-1-yl)imidazole-5-carboxylate. $^1$H-NMR (CDCl$_3$) 5.85 (s, 2H), 3.68 (s, 3H), 2.0 (s, 6H), 1.80–2.0 (m, 1H), 1.0–1.18 (m, 4H).

EXAMPLE 42

Methyl 2-cyclopropyl-4-(2,5-dimethyl-1H-pyrrol-1-yl)-1-[(2'-(1H-tetrazol-5-yl)biphen-4-yl)methyl]-1H-imidazole-5-carboxylate Using an analogous procedure to that described in Example 13, but starting from methyl 2-cyclopropyl-4-(2,5-dimethyl-1H-pyrrol-1-yl)imidazole-5-carboxylate (Example 41) was obtained the title compound methyl 2-cyclopropyl 4-(2,5-dimethyl-1H-pyrrol-1-yl)-1-[(2'-(1H-tetrazol-5-yl)biphen-4-yl)methyl]-1H-imidazole-5-carboxylate. MS (CI, CH$_4$+NH$_3$) 494(M+).

EXAMPLE 43

2-Cyclopropyl-4-(2,5 dimethyl-1H-pyrrol-1-yl)-1-[(2'-1H-tetrazol-5-yl)biphen-4-yl)methyl]-1H-imidazole-5- o carboxylic acid To a solution of methyl 2-cyclopropyl-4-(2,5 dimethyl-1H-pyrrol-1-yl)-1 [(2'-(1H-tetrazol-5-yl)biphen-4-yl)methyl]-1H-imidazole-5-carboxylate (Example 42, 1.91 g) in anhydrous THF was added potassium trimethylsilanolate (1.57 g) and the mixture stirred at ambient temperature for 20 hours. The solvent was removed under reduced pressure and the residue taken up in water (25 mL). The aqueous solution was filtered and extracted with ethyl acetate. The aqueous layer was acidified to pH 4.5 with 1N HCl and extracted with ethyl acetate. The combined organic extracts were dried over anhydrous magnesium sulfate and evaporated to give the title compound 2-cyclopropyl-4-(2,5-dimethyl-1H-pyrrol-1-yl)-1-[(2'-(1H-tetrazol-5-yl)biphen-4-yl)methyl]-1H-imidazole-5-carboxylic acid. MS (CI, CH$_4$+NH$_3$) 480 (M+).

EXAMPLE 44

Methyl 4-(2-methyl-5-propyl-1H-pyrrol-1-yl)-2-propylimidazole-5-carboxylate

Using an analogous procedure to that described in Example 41, but starting from 2,5-octanedione was obtained the title compound methyl 4-(2 methyl-5-propyl-1H-pyrrol-1-yl)-2-propyl-imidazole-5-carboxylate. $^1$H-NMR (CDCl$_3$) 5.90 (s, 2H), 3.70 (s, 3H), 2.75 (t, 2H), 2.30 (t, 2H), 2.0 (s, 3H), 1.90–1.70 (m, 2H), 1.58–1.35 (m, 2H), 0.98( t, 3H), 0.8 (t, 3H).

EXAMPLE 45

Methyl 4-(2-methyl-5-propyl-1H-pyrrol-1-yl)-2-propyl-1-[(2'-(1H-tetrazol-5-yl)biphen-4-yl)methyl]-1H-imidazole-5-carboxylate Using an analogous procedure to that described in Example 13, but starting from methyl 4-(2-methyl-5-propyl-1H-pyrrol-1-yl)-2-propyl-imidazole-5-carboxylate (Example 44) was obtained the title compound methyl 4-(2-methyl-5-propyl-1H-pyrrol-1-yl)-2-propyl-1-[(2'-(1H-tetrazol-5-yl)biphen-4-yl)methyl]-1H-imidazole 5-carboxylate, mp 95°–101° C. MS (DEI) 523(M+) 524(M+1).

EXAMPLE 46

4-(2-Methyl-5-propyl-1H-pyrrol-1-yl)-2-propyl-1-[(2'-(1H-tetrazol-5-yl)biphen-4-yl)methyl]-1H-imidazole-5-carboxylic acid Using an analogous procedure to that described in Example 43, but starting from methyl 4-(2-methyl-5-propyl-1H-pyrrol-1-yl)-2-propyl-1-[(2'-(1H-tetrazol-5-yl)biphen-4-yl)methyl]-1H-imidazole-5-carboxylate (Example 45) was obtained the title compound 4-(2-methyl-5-propyl-1H-pyrrol-1-yl)-2-propyl-1-[(2'-(1H-tetrazol-5-yl)biphen-4-yl)-methyl]-1H-imidazole 5-carboxylic acid. MS (DEI) 523(M+) 524(M+1).

EXAMPLE 47

Methyl 4-(2,5-dimethyl-1H-pyrrol-1-yl)-2-propylimidazole-5-carboxylate

Using an analogous procedure to that described in Example 41, but starting from methyl 4-amino 2-propylimidazol-5-carboxylate (Example 4) provided the title compound methyl 4-(2,5-dimethyl-1H-pyrrol-1-yl)-2-propyl-midazole-5-carboxylate, mp 175°–176° C.

EXAMPLE 48

5-(Hydroxymethyl)-2-propyl-4-(2,5-dimethyl-1H-pyrrol-1-yl)imidazole

Using an analogous procedure to that described in Example 29, but starting from methyl 4-(2,5-dimethyl-1H-pyrrol-1-yl)-2-propyl-imidazole-5-carboxylate (Example 47) was obtained the title compound 5-(hydroxy methyl)-2-propyl-4-(2,5-dimethyl-1H-pyrrol-1-yl)imidazole. MS (DEI) 233(M+) 234(M+1).

EXAMPLE 49

4-(2,5-Dimethyl-1H-pyrrol-1-yl)-2-propylimidazole-5-carboxaldehyde

To a solution of 5-(hydroxy-methyl)-2-propyl-4-(2,5-dimethyl-1H-pyrrol-1-yl)imidazole (Example 48, 6.0 g, 0.026 mol) in dry THF (125 mL) was added MnO$_2$ (11.2 g, 0.13 mol) and the reaction mixture refluxed for 4 hours under an atmosphere of nitrogen. The reaction mixture was cooled, filtered through celite, and the resulting filtrate evaporated under reduced pressure. Purification by flash chromatography (silica; 2:1 hexane ethyl acetate) gave the title compound 4-(2,5-dimethyl-1H-pyrrol 1-yl)-2-propylimidazole-5-carboxaldehyde (4.5 g, 75%), mp 119°–121° C.

EXAMPLE 50

4-(2,5-Dimethyl-1H-pyrrol-1-yl)-2-propyl-1-[[2'-(N-triphenylmethyl-tetrazol-5-yl)-1,1'-biphenyl-4-yl]methyl]-1H-imidazole-5-carboxaldehyde A mixture of N-(triphenylmethyl)-5-[4'-(bromomethyl)-biphenyl-2-yl]tetrazole (Example 12, 9.66 g, 17.34 mmol), 4-(2,5-dimethyl-1H-pyrrol-1-yl)-2-propyl-1H-imidazole-5-carboxaldehyde (Example 49, 4.0 g, 17.4 mmol), and cesium carbonate (13 g, 40 mmol) in DMF (30 mL) was stirred under an atmosphere of dry nitrogen at room temperature overnight. The reaction mixture was poured over water (750 mL) and the resulting precipitate was collected by filtration. The solid was taken up in ethyl acetate and extracted with water, adjusting the pH of the aqueous layer to pH 8–9 by the addition of sodium bicarbonate. The organic layer was dried over $MgSO_4$ and evaporated to give the crude product as a mixture of regioisomers which were separated by flash chromatography (silica; 3:1 hexane/EtOAc).

High Rf regioisomer:
4-(2,5-dimethyl-1H-pyrrol-1-yl)-2-propyl-1-[[2'-(N-triphenylmethyl-tetrazol-5-yl)-1,1'-biphenyl-4-yl]methyl]-1H-imidazole-5-carboxaldehyde. $^1$H-NMR (DMSO-$d_6$) 5.62 (s, 2H, benzylic $CH_2$)

Analysis for $C_{46}H_{41}N_7O$: Calc.: C, 78.05; H, 5.84; N, 13.85. Found: C, 77.64; H, 5.65; N, 13.65.

EXAMPLE 51

Methyl (E)-3-[4-(2,5-dimethyl-1H-pyrrol-1-yl)-2-propyl-1-[[2'-2-(triphenylmethyl)-2H-tetrazol-5-yl]-1,1'-biphenyl-4-yl]methyl]-1H-imidazol-5-yl]-2-propenoate A solution of 4-(2,5-dimethyl-1H-pyrrol-1-yl)-2-propyl-1-[[2'-(N-tri-phenylmethyl-tetrazol-5-yl)-1,1'-biphenyl-4-yl]methyl]-1H-imidazole-5-carboxaldehyde (Example 50, 5 g) and (carbomethoxymethylene)triphenylphosphorane (13 g) in toluene (50 mL) was heated at reflux for 30 minutes. The reaction mixture was cooled and filtered and the filtrate was concentrated on the rotovap.

Purification of the residue by flash chromatography (silica; 2:1 hexane/EtOAc) gave the pure (E)-isomer (2.7 g) as an oil.

Analysis for $C_{49}H_{45}N_7O_2$: Calc.: C, 77.04; H, 5.94; N, 12.83. Found: C, 77.02; H, 5.76; N, 12.70.

EXAMPLE 52

Methyl (E)-3-[4-(2,5-dimethyl-1H-pyrrol-1-yl)-2-propyl-1-[[2'-(1H-tetrazol-5-yl)-1,1'-biphenyl-4-yl]methyl]-1H-imidazol-5-yl]-2-propenoate A solution of methyl (E)-3-[4-(2,5-dimethyl-1H-pyrrol-1-yl)-2-propyl-1-[[2,'-2-(tri-phenylmethyl)-2H-tetrazol-5-yl]-1,1'-biphenyl-4-yl]methyl]-1H-imidazol-5-yl]-2-propenoate (Example 51, 1.0 g) in 100 mL methanol was treated with 10% aqueous citric acid (20 mL) and the resulting mixture was heated at reflux for 30 minutes. The reaction mixture was cooled, diluted with 20 mL water and extracted with hexane. The methanol layer was collected and concentrated to 50 mL on the rotovap. It was diluted with water and the resulting precipitate was collected by filtration. Recrystallization from isopropyl ether gave pure deprotected tetrazole (490 mg), mp 212-213° C.

Analysis for $C_{30}H_{31}N_7O_2$: Calc.: C, 69.08; H, 5.99; N, 18.80. Found: C, 69.24; H, 6.15; N, 18.59.

EXAMPLE 53

(E)-3-[4-(2,5-Dimethyl-1H-pyrrol-1-yl)-2-propyl-1-[2'-(1H-tetrazol-5-yl)-1,1'-biphenyl-4-yl]methyl]-1H-imidazol-5-yl]-2-propenoic acid A solution of methyl (E)-3-[4-(2,5-dimethyl-1H-pyrrol-1-yl)-2-propyl-1-[[2'-(1H-tetrazol-5-yl) 1,1'-biphenyl-4-yl]methyl]-1H-imidazol-5-yl]-2-propenoate (Example 52, 1.55 g, 3 mmol), and potassium trimethylsilanolate (0.96 g, 7.5 mmol) in dry THF (80 mL) was stirred at room temperature for 3 hours under an atmosphere of dry nitrogen. The resulting precipitate was collected by filtration, air dried, and then dissolved in water (50 mL). The free acid was precipitated out by the addition of 1N HCl and collected by filtration giving (E)-3-[4-(2,5-dimethyl-1H-pyrrol-1-yl)-2-propyl-1-[[2'-(1H-tetrazol-5-yl)-1,1'-biphenyl-4-yl]methyl]-1H-imidazol-5-yl]-2-propenoic acid (1.3 g, 83%) as a partial hydrate, mp 144 150° C.

Analysis for $C_{29}H_{29}N_7O_2 \cdot 0.7H_2O$: Calc.: C, 66.84; H, 5.90; N, 18.81. Found: C, 66.94; H, 5.82; N, 18.72.

EXAMPLE 54

5-(Hydroxymethyl)-2-propyl-4-(1H-pyrrol-1-yl)imidazole

Using an analogous procedure to that described in Example, 29, but starting from methyl 2-propyl-4-(1H-pyrrol-1-yl)imidazol-5-carboxylate (Example 5) the title compound 5 (hydroxymethyl)-2-propyl-4-(1H-pyrrol-1-yl)imidazole was obtained, mp 155°–158° C.

EXAMPLE 55

2-Propyl-4-(1H-pyrrol-1-yl)-imidazole-5-carboxaldehyde

Using an analogous procedure to that described in Example 49, but starting from 5-(hydroxymethyl)-2-propyl-4-(1H-pyrrol-1-yl)imidazole (Example 54) was obtained the title compound 2-propyl-4-(1H-pyrrol-1-yl)-imidazole-5-carboxaldehyde, mp 118.5°–120° C.

EXAMPLE 56

4-(1H-Pyrrol-1-yl)-2-propyl-1-[[2'-(N-triphenylmethyl-tetrazol-5-yl)-1,1'-biphenyl-4-yl]methyl]-1H-imidazole-5-carboxaldehyde Using an analogous procedure to that described pyrrol-1-yl)-imidazole-5-carboxaldehyde (Example 55) was obtained the title compound 4-(1H-pyrrol-1-yl)-2-propyl-1-[[2'-(N-tri-phenylmethyl-tetrazol-5-yl)-1,1'-biphenyl-4-yl]methyl]-1H-imidazole-5-carboxaldehyde which was used in the next step without further purification.

EXAMPLE 57

Ethyl (E)-3-[4-(1H-pyrrol-1-yl)-2-propyl-1-[2'-2-(triphenylmethyl)-2H-tetrazol-5-yl]-1,1'-biphenyl-4-yl]methyl]-1H-imidazol-5-yl]-2-propenoate Using an analogous procedure to that described in Example 51, but starting from 4-(1H-pyrrol-1-yl)-2-propyl-1-[[2'-(N-tri-phenylmethyl-tetrazol-5-yl)-1,1'biphenyl-4-yl]methyl]-1H-imidazole-5-carboxaldehyde (Example 56) and (carbethoxymethylene)triphenylphosphorane was obtained the title compound ethyl (E)-3-[4-(1H-pyrrol-1-yl)-2-propyl-1-[[2'-2-(triphenylmethyl)-

2H tetrazol-5-yl]-1,1'-biphenyl-4-yl]methyl]-1H-imidazol-5-yl]-2-propenoate which was used directly in the next step.

EXAMPLE 58

Ethyl (E)-3-[4-(1H-pyrrol-1-yl)-2-propyl-1-[[2-(1H-tetrazol-5-yl)-1,1'-biphenyl-4-yl]methyl]-1H-imidazol-5-yl]-2-propenoate Using an analogous procedure to that described in Example 52, but starting from ethyl (E)-3-[4-(1H-pyrrol-1-yl)-2-propyl-1-[[2'-2-(triphenylmethyl)-2H-tetrazol-5-yl]-1,1'-biphenyl-4-yl]methyl]-1H-imidazol-5-yl]-2-propenoate (Example 57) afforded the title compound ethyl (E)-3-[4-(1H-pyrrol-1-yl)-2-propyl-1-[[2'-(1H-tetrazol-5-yl)-1,1'-biphenyl-4yl]methyl]-1H-imidazol-5-yl]-2-propenoate which was hydrolyzed to the directly to the acid in the next step.

EXAMPLE 59

(E)-3-[4-(1H-Pyrrol-1-yl)-2-propyl-1-[[2'-(1H-tetrazol-5-yl)-1,1'-biphenyl-4-yl]methyl]-1H-imidazol-5-yl]-2-propenoic acid Using an analogous procedure to that described in Example 53, but starting from ethyl (E)-3-[4-(1H-pyrrol-1-yl)-2-propyl-1-[[2'-(1H-tetrazol-5-yl)-1,1'-biphenyl-4-yl]methyl]-1H-imidazol-5-yl]-2-propenoate (Example 53) was obtained the title compound (E) 3-[4-(1H-pyrrol-1-yl)-2-propyl-1-[[2'-(1H-tetrazol-5-yl)-1,1'-biphenyl-4-yl]methyl]-1H-imidazol-5-yl]-2-propenoic acid. MS (FAB, thioglycerol) 480 (M+1) 588 (M+thioglycerol).

EXAMPLE 60

Ethyl (E)-2-methyl-3-4-(1H-pyrrol-1-yl)-2-propyl-1-[2'-2-(tri-phenylmethyl)-2H-tetrazol-5-yl]-1,1'-biphenyl-4-yl]methyl]-1H-imidazol-5-yl]-2-propenoate Using an analogous procedure to that described in Example 51, but starting from 4-(1H-pyrrol-1-yl)-2-propyl-1-[[2'-(N-tri-phenylmethyl-tetrazol-5-yl)-1,1'-biphenyl-4-yl]methyl]-1H-imidazole-5-carboxaldehyde (Example 56) and (carbethoxy ethylidene)triphenylphosphorane was obtained the title compound ethyl (E)-2-methyl-3-[4-(1H-pyrrol-1-yl)-2 propyl-1-[[2'-2-(tri-phenylmethyl)-2H-tetrazol-5-yl]-1,1'-biphenyl-4-yl]methyl]-1H-imidazol-5-yl]-2-propenoate. MS (FAB, thioglycerol) 764(M+1).

EXAMPLE 61

Ethyl (E)-2-methyl-3-4-(1H-pyrrol-1-yl)-2-propyl-1-[[2'-(1H-tetrazol-5-yl)-1,1'-biphenyl-4-yl]methyl]-1H-imidazol-5-yl]-2-propenoate Using an analogous procedure to that described in Example 52, but starting from ethyl (E)-2-methyl-3-[4-(1H-pyrrol-1-yl)-2-propyl-1-[[2'-2-(triphenylmethyl)-2H-tetrazol-5-yl]-1,1'-biphenyl-4-yl]methyl]1H-biphenyl-5-yl]-2-propenoate (Example 60) afforded the title compound ethyl (E)-2-methyl-3-[4-(1H-pyrrol-1-yl)-2-propyl-1-[[2'-(1H-tetrazol-5-yl)-1,1'-biphenyl-4-yl]methyl]-1H-imidazol-5-yl]-2-propenoate. MS (CI, CH$_4$+NH$_3$) 522(M+1).

EXAMPLE 62

(E)-2-Methyl-3-[4-(1H-pyrrol-1-yl)-2-propyl-1-[[2'-(1H-tetrazol-5-yl)-1,1'-biphenyl-4-yl]methyl]-1H-imidazol-5-yl]-2-propenoic acid Using an analogous procedure to that described in Example 53, but starting from ethyl (E)-2-methyl-3-[4-(1H-pyrrol-1-yl)-2-propyl-1-[[2'-(1H-tetrazol-5-yl)-1,1'-biphenyl-4-yl]methyl]-1H-imidazol-5-yl]-2-propenoate (Example 61) was obtained the title compound (E)-2-methyl-3-[4-(1H-pyrrol-1-yl)-2-propyl-1-[[2'-(1H-tetrazol-5-yl)-1,1'-biphenyl-4-yl]methyl]-1H-imidazol-5-yl]-2-propenoic acid. MS (CI, CH$_4$+NH$_3$) 494 (M+1).

EXAMPLE 63

4-(2,5-Dimethyl-1H-pyrrol-1-yl)-2-propyl-1-[[2'-(1H-tetrazol-5-yl)-1,1'-biphenyl-4-yl]methyl]-1H-imidazole-5-carboxaldehyde Prepared from 4-(2,5-dimethyl-1H-pyrrol-1-yl)-2-propyl-1-[[2'-(N-triphenylmethyl-tetrazol-5-yl)-1,1'-biphenyl-4-yl]methyl]-1H-imidazole-5-carboxaldehyde according to the procedure of Example 52. MS (EI, CH$_4$+NH$_3$) 465 (M+).

EXAMPLE 64

Methyl 4-(2-methyl-3-carboxymethyl-1H-pyrrol-1-yl)-2-propylimidazole-5-carboxylate Using an analogous procedure to that described in Example 5, but starting from methyl 4-amino-2-propylimidazol-5-carboxylate (Example 4) and methyl 5-acetoxy-2-methyl-4,5-dihydrofuran-3-carboxylate (*Synthetic Communications* 20(13):1923–1929 (1990)) afforded the title compound methyl 4-(2-methyl-3-carboxymethyl-1H-pyrrol-1-yl)-2-propylimidazole-5-carboxylate, mp 161°–162° C.

Anal for C$_{15}$H$_{19}$N$_3$O$_4$: Calc.: C, 59.01; H, 6.27; N, 13.76. Found: C, 58.85; H, 6.44; N, 13.59. MS (CI, CH$_4$+NH$_3$) 305 (M+).

EXAMPLE 65

Methyl 4-(3-carboxymethyl-2-methyl-1H-pyrrol-1-yl)-2-propyl-1-(2'-(2-triphenylmethyl-2H-tetrazol-5-yl)biphen-4-yl)methyl]-1H-imidazole-5-carboxylate Using an analogous procedure to that described in Example 50, but starting from methyl 4-(2-methyl-3-carboxymethyl-1H-pyrrol-1-yl)-2-propylimidazole-5-carboxylate (Example 64) afforded the title compound methyl 4-(3-carboxymethyl-2-methyl-1H-pyrrol-1-yl)-2-propyl-1-[(2'-(2-tri-phenylmethyl-2H-tetrazol-5-yl)biphen-4-yl)methyl]-1H-imidazole-5-carboxylate. MS (FAB, thioglycerol) 782 (M+).

EXAMPLE 66

Methyl 4-(3-carboxymethyl-2-methyl-1H-pyrrol-1-yl)-2-propyl-1-[(2'-(1H-tetrazol-5-yl)biphen-4-yl)methyl]-1H-imidazole-5-carboxylate Using an analogous procedure to that described in Example 52, but starting from methyl 4 (3-carboxymethyl-2-methyl-1H-pyrrol-1-yl)-2-propyl-1-[(2'-(2-triphenylmethyl-2H-tetrazol-5-yl)biphen-4-yl)methyl]-1H-imidazole-5-carboxylate (Example 65) afforded the title compound methyl 4-(3-carboxymeth yl-2-methyl-1H-pyrrol-1-yl)-2-propyl-1-[(2'-(1H-tetrazol-5-yl)-biphen-4-yl)methyl]-1H-imidazole-5-carboxylate. MS (CI, $CH_4+NH_3$) 540 (M+).

EXAMPLE 67

4-(3-Carboxymethyl-2-methyl-1H-pyrrol-1-yl)-2-propyl-1-(2'-(1H-tetrazol-5-yl)biphen-4-yl)methyl]-1H-imidazole-5-carboxylic acid and 4-(3-carboxy-2-methyl-1H-pyrrol-1-yl)-2-propyl-1-[(2'-(1H-tetrazol-5-yl)biphen-4-yl)methyl]-1H-imidazole-5-carboxylic acid To a solution of methyl 4-(3-carboxymethyl-2-methyl-1H-pyrrol-1-yl)-2-propyl-1-[(2'-(1H-tetrazol-5-yl)biphen-4-yl)methyl]-1H-imidazole-5-carboxylate (Example 66, 1.98 g) in methanol (10 mL) was added 2N KOH (4.5 mL) and the reaction mixture heated under reflux for 4 hours. The solvent was diluted with water and acidified with 1N HCl and the crude mixture of products collected by filtration. Purification by chromatography over silica gel eluting with $CH_2Cl_2$/MeOH/AcOH (9/1/0.1) afforded two products in order of elution:

A) 4-(3-carboxymethyl-2-methyl-1H-pyrrol-1-yl)-2-propyl-1-[(2'-(1H-tetrazol-5-yl)biphen-4-yl)methyl]-1H-imidazole-5-carboxylic acid (0.5 g). MS (CI, $CH_4+NH_3$) 482 (m-$CO_2$).

B) 4-(3-carboxy-2-methyl-1H-pyrrol-1-yl)-2-propyl-1-[(2'-(1H-tetrazol-5-yl)biphen-4-yl)methyl]-1H-imidazole-5-carboxylic acid (1.05 g). MS (FAB, thioglycerol) 512 (M+).

EXAMPLE 68

Methyl 4-(2,5-dimethyl-1H-pyrrol-1-yl)-2-propylimidazole-5-carboxylate

Using an analogous procedure to that described in Example 41, but starting from methyl 4-amino-2-propylimidazol-5-carboxylate (Example 4) was obtained the title compound methyl 4-(2,5-dimethyl-1H-pyrrol-1-yl)-2-propylimidazole-5-carboxylate.

Anal for $C_{14}H_{19}N_3O_2$: Calc.: C, 64.35; H, 7.33; N, 16.08. Found: C, 64.64; H, 7.52; N, 16.08. MS (CI, $CH_4+NH_3$) 261 (M+).

EXAMPLE 69

Methyl 4-(2,5-dimethyl-1H-pyrrol-1-yl)-2-propyl-1-[(2'-(2-triphenylmethyl-2H-tetrazol-5-yl)biphen-4-yl)methyl]-1H-imidazole-5-carboxylate Using an analogous procedure to that described in Example 50, but starting from methyl 4-(2,5-dimethyl-1H-pyrrol-1-yl)-2-propylimidazole-5-carboxylate (Example 68) afforded the title compound methyl 4-(2,5-dimethyl-1H-pyrrol-1-yl)-2-propyl-1-[(2'-(2-triphenyl-methyl-2H-tetrazol-5-yl)biphen-4-yl)methyl]-1H-imidazole-5-carboxylate. MS (FAB, thioglycerol) 738 (M+).

EXAMPLE 70

Methyl 4-(2,5-dimethyl-1H-pyrrol-1-yl)-2-propyl-1-[(2'-(1H-tetrazol-5-yl)biphen-4-yl)methyl]-1H-imidazole-5-carboxylate Using an analogous procedure to that described in Example 50, but starting from methyl 4-(2,5-dimethyl-1H-pyrrol-1-yl)-2-propyl-1-[(2'-(2-triphenylmethyl-2H-tetrazol-5-yl)biphen-4-yl)methyl]-1H-imidazole-5-carboxylate (Example 69) was obtained the title compound methyl 4-(2,5-dimethyl-1H-pyrrol-1yl)-2-propyl-1-[(2'-(1H-tetrazol-5-yl)biphen-4-yl)methyl]-1H-imidazole-5-carboxylate.

Anal for $C_{28}H_{29}N_7O_2 \cdot CH_3OH$: Calc.: C, 66.02; H, 6.30; N, 18.58. Found: C, 65.93; H, 5.92; N, 18.25. MS (FAB, thioglycerol) 496 (M ).

EXAMPLE 71

4-(2,5-Dimethyl-1H-pyrrol-1-yl)-2-propyl-1-(2'-(1H-tetrazol-5-yl)biphen 4-yl)methyl]-1H-imidazole-5-carboxylic acid A mixture of methyl 4-(2,5-dimethyl-1H-pyrrol-1-yl)-2-propyl-1-[(2'-(1H-tetrazol-5-yl)biphen-4-yl)methyl]-1H-imidazole-5-carboxylate 9 (Example 70) in methanol (5 mL) containing 5 mL of 2.5N NaOH was heated under reflux for 3 hours. The reaction mixture was cooled, acidified with 10% citric acid to pH 4, and extracted with ethyl acetate. The combined organic layers were dried over anhydrous $MgSO_4$ and the solvent removed under reduced pressure. The acid was further purified by flash chromatography on silica gel eluting with 5% methanol in ethyl acetate to furnish 0.2 g for the title compound 4-(2,5-dimethyl-1H-pyrrol-1-yl)-2-propyl-1-[(2'-(1H-tetrazol-5-yl)biphen-4-yl)methyl]-1H-imidazole-5-carboxylic acid. MS (FAB, thioglycerol) 482 (M+).

EXAMPLE 72

Methyl 4-(3-carboxyethyl-1H-pyrrol-1-yl)-2-propylimidazole-5-carboxylate

Using an analogous procedure to that described in Example 5, but starting from methyl 4-amino-2-propylimidazol-5-carboxylate (Example 4) and 3-carboethoxy-2,5-dimethoxytetrahydrofuran (prepared by the method of Niels Clauson-Kaas, *Acta Chem. Scand.* 6:556–559 (1952)) afforded the title compound methyl 4-(3-carboxyethyl-1H-pyrrol-1-yl)-2-propylimidazole-5-carboxylate. MS (CI, $CH_4+NH_3$) 305 (M+) 306 (M+1).

EXAMPLE 73

Methyl 4-(3-carboxyethyl-1H-pyrrol-1-yl)-2-propyl-1-[(2'-(1H-tetrazol-5-yl)biphen-4-yl)methyl]-1H-imidazole-5-carboxylate Using an analogous procedure to that described in Example 13, but starting from 4-(3-carboxyethyl-1H-pyrrol-1-yl)-2-propylimidazole-5-carboxylate (Example 72) afforded the title compound methyl 4-(3-carboxyethyl-1H-pyrrol-1-yl)-2-propyl-1-[(2'-(1H-tetrazol-5-yl)biphen-4-yl)methyl]-1H-imidazole-5-carboxylate.

Anal for $C_{29}H_{29}N_7O_2$: Calc.: C, 64.55; H, 5.42; N, 18.17. Found: C, 64.68; H, 5.35; N, 18.56. MS (CI, $CH_4+NH_3$) 539 (M+).

EXAMPLE 74

4-(3-Carboxyethyl-1H-pyrrol-1-yl)-2-propyl-1-(2'-(1H-tetrazol-5-yl)biphen-4-yl)methyl]-1H-imidazole-5-carboxylic acid A solution of methyl 4-(3-carboxyethyl-1H-pyrrol-1-yl)-2-propyl-1-[(2'-(1H-tetrazol-5-yl)-biphen-4-yl)methyl]-1H-imidazole-5-carboxylate (Example 73, 0.2 g) in ethanol (2.5 mL) and water (1.25 mL) was treated with lithium hydroxide (0.17 g) ant the reaction mixture stirred a room temperature for 3 days. The reaction mixture was diluted with water, extracted with ether, and the aqueous layer acidified to pH 2 with 1N HCl. The cloudy solution was extracted with ether and the combined organic layers dried over anhydrous magnesium sulfate. The solvent was evaporated under reduced pressure and the residue taken-up in ethyl acetate. Petroleum ether was added dropwise to precipitate the product which was collected by filtration to yield 0.11 g of the title compound 4-(3-carboxyethyl-1H-pyrrol-1-yl)-2-propyl-1-[(2'-(1H-tetrazol-5-yl)biphen-4-yl)methyl]-1H-imidazole-5-carboxylic acid. MS (CI, $CH_4+NH_4$) 410 (M-$CO_2H$, —$CO_2Et$).

EXAMPLE 75

(3-Carboxy-1pyrrol-1-yl)-2-propyl-1-(2'-(1H-tetrazol-5-yl)biphen-4-yl)methyl]-1H-imidazole-5-carboxylic acid Using an analogous procedure to that described in Example 71, but starting from methyl 4-(3-carboxyethyl-1H-pyrrol-1-yl)-2-propyl-1-[(2'-(1H-tetrazol-5-yl)biphen-4-yl)methyl]-1H-imidazole-5-carboxylate (Example 73) afforded the title compound 4-(3-carboxy-1H-pyrrol-1-yl)-2-propyl-1-[(2'-(1H-tetrazol-5-yl)biphen-4-yl)methyl]-1H-imidazole-5-carboxylic acid. MS (CI, $CH_4+NH_4$) 410 (M- $2CO_2H$).

EXAMPLE 76

4-(2,5-Dimethyl-1H-pyrrol-1-yl)-5-(hydroxymethyl)-2-propyl-1-[(2'-(2-triphenylmethyl-2H-tetrazol-5-yl)biphen-4-yl)methyl]-1H-imidazole To a solution of methyl 4-(2,5-dimethyl-1H-pyrrol-1-yl)-2-propyl-1-[(2'-(2-triphenyl-methyl-2H-tetrazol-5-yl)biphen-4-yl)methyl]-1H-imidazole-5-carboxylate (Example 69, 1.0 g) in THF (12 mL) was added dropwise 1.5 mL of a 1M solution of LAH in ether. The reaction mixture was stirred overnight then quenched with aqueous ammonium sulfate. The resulting suspension was filtered and the insoluble material washed with hot ethyl acetate. The filtrate was separated and the organic layer extracted with brine. The organic layer was dried over anhydrous magnesium sulfate and evaporated under reduced pressure. The crude product was purified by flash chromatography eluting with 5% acetone in $CH_2Cl_2$ to afford title compound 4-(2,5-dimethyl-1H-pyrrol-1-yl)-5-(hydroxymethyl)-2-propyl-1-[(2'-(2-triphenylmethyl-2H-tetrazol-5-yl)-4-yl)methyl]-1H-imidazole, mp 185°–186° C.

EXAMPLE 77

4-(2,5-Dimethyl-1H-pyrrol-1-yl)-5-(hydroxymethyl)-2-propyl-1-(2'-(1H-tetrazol-5-yl)biphen-4-yl)methyl]-1H-imidazole Using an analogous procedure to that described in Example 52, but starting from 4-(2,5-dimethyl-1H-pyrrol-1-yl)-5-(hydroxymethyl)-2-propyl-1-[(2'-(2-triphenylmethyl-2H-tetrazol-5-yl)biphen-4-yl)methyl]-1H-imidazole (Example 76) was obtained the title compound 4-(2,5-dimethyl-1H-pyrrol-1-yl)-5-(hydroxymethyl)-2-propyl-1-[(2'-(1H-tetrazol-5-yl)biphen-4-yl)methyl]-1H-imidazole.

EXAMPLE 78

Methyl 2-propyl-4-(2,5-dichloro-1H-pyrrol-1-yl)imidazole-5-carboxylate

Using an analogous procedure to that described in Example 30, but starting from methyl 2-propyl-4-(1H-pyrrol-1-yl)imidazole-5-carboxylate (Example 5) was obtained the title compound methyl 2-propyl-4-(2,5-dichloro-1H-pyrrol-1-yl)imidazole-5-carboxylate.

EXAMPLE 79

Methyl 4-(2,5-dichloro-1H-pyrrol-1-yl)-2-propyl-1-[(2'-(1H-tetrazol-5-yl)biphen-4-yl)methyl]-1H-imidazole-5-carboxylate Using an analogous procedure to that described in Example 13, but starting from methyl 2-propyl-4-(2,6-dichloro-1H-pyrrol-1-yl)imidazole-5-carboxylate (Example 77) was obtained the title compound methyl 4-(2,5-dichloro-1H-pyrrol-1-yl)-2-propyl-1-[(2'-(1H-tetrazol-5-yl)biphen-4-yl)methyl]-1H-imidazole-5-carboxylate.

EXAMPLE 80

4-(2,5-Dichloro-1H-pyrrol-1-yl)-2-propyl-1-[(2'-(1H-tetrazol-5-yl)biphen-4-yl)methyl]-1H-imidazole-5-carboxylic acid Using an analogous procedure to that described in Example 14, but starting from methyl 4-(2,5-dichloro-1H-pyrrol-1-yl)-2-propyl-1-[(2'-(1H-tetrazol-5-yl)biphen-4-yl)methyl]-1H-imidazole-5-carboxylate (Example 79) was obtained the title compound 4 (2,5-dichloro-1H-pyrrol-1-yl)-2-propyl-1-[(2'-(1H-tetrazol-5-yl)biphen-4-yl)methyl]-1H-imidazole-5-carboxylic acid.

EXAMPLE 81

Methyl 2-butyl-4-[2-(1-oxo-2,2,2-trifluoroethyl)-1H-pyrrol-1-yl]-1-[(2'-(1H-tetrazol-5-yl)biphen-4-yl)methyl]-1H-imidazole-5-carboxylate Using an analogous procedure to that described in Example 13, but starting from methyl 2-butyl-4-[2-(1-oxo-2,2,2-trifluoroethyl)-1H-pyrrol-1-yl]imidazol-5-carboxylate was obtained the title compound methyl butyl-4-[2-(1-oxo-2,2,2-trifluoroethyl)-1H-pyrrol-1-yl]-1-[(2'-(1H-tetrazol-5-yl)biphen-4-yl)methyl]-1H-imidazole-5-carboxylate, mp 91°–96° C. MS (CI, $CH_4+NH_3$) 592 (M+$CH_3$).

EXAMPLE 82

2-Butyl-4-[2-(1-oxo-2,2,2-trifluoroethyl)-1H-pyrrol-1-yl]-1-[2'-(1H-tetrazol-5-yl)biphen-4-yl)methyl]-1H-imidazole-5-carboxylic acid Using an analogous procedure to that described in Example 14, but starting from methyl 2-butyl-4-[2-(1-oxo-2,2,2-trifluoroethyl)-1H-pyrrol-1-yl]-1-[(2'-(1H-tetrazol-5-yl)biphen-4-yl)methyl]-1H-imidazole-5-carboxylate (Example 81) was obtained the title compound 2-butyl-4-[2-(1-oxo-2,2,2-trifluoroethyl)-1H-pyrrol-1-yl]-1-[(2'-(1H-tetrazol-5-yl)biphen-4-yl)methyl]1H-imidazole-5-carboxylic acid, mp 160°–173° C. MS (FAB, thioglycerol) 564(M+1).

We claim:
1. A compound selected from
4-amino-2-butyl-5-cyanoimidazole,
4-amino-5-cyano-2-propylimidazole,
2-butyl-5-cyano-4-(1H-pyrrol-1-yl)imidazole,
5-cyano-2-propyl-4-(1H-pyrrol-1-yl)imidazole,
ethyl 2-butyl-4-(1H-pyrrol-1-yl)imidazole-5-carboxylate, methyl 2-butyl-4-(1H-pyrrol-1-yl)imidazole, 2-butyl-5-(hydroxymethyl)-4-(1H-pyrrol-1-yl)imidazole-5-carboxylate, 5-cyano-4-[2-(1-oxo-2,2,2-trifluoroethyl)-1H-pyrrol-1-yl]-2-propylimidazole, methyl 1-(5-cyano-2-propylimidazol-4-yl)1H-pyrrole-2-carboxylate, 5-cyano-4-(2,5-dichloro-1H-pyrrol-1-yl)-2-propylimidazole, methyl 4-[2-(1-oxo-2,2,2-trifluoroethyl)-1H-pyrrol-1-yl]-2-propylimidazole-5-carboxylate, methyl 2-butyl-4-[2-(1-oxo-2,2,2-trifluoroethyl)-1H-pyrrol-1-yl]imidazole-5-carboxylate, 5-cyano-4-(2,5-dichloro-1H-pyrrol-1-yl)-2-propylimidazole, methyl 2-cyclopropyl-4-(2,5-dimethyl-1H-pyrrol-1-yl)-imidazole-5-carboxylate, methyl 4-(2-methyl-5-propyl-1H-pyrrol-1-yl)-2-propylimidazole-5-carboxylate, 4-(2,5-dimethyl-1H-pyrrol-1-yl)-2-propylimidazole-5-carboxylate, methyl 4-(3-carboxyethyl-1H-pyrrol-1-yl)-2-propylimidazole-5-carboxylate, methyl 4-(2,5-dimethyl-1H-pyrrol-1-yl)-2-propylimidazole-5-carboxylate, 2-propyl-4-(1H-pyrrol-1-yl)-imidazole-5-carboxaldehyde, 5-(hydroxymethyl)-2 propyl-4-(1H-pyrrol-1-yl)imidazole, 2-butyl-5-(hydroxymethyl)-4-(1H-pyrrol-1-yl)imidazole, 5-cyano-4-(2,5-dimethyl-1H-pyrrol-1-yl)-2-propylimidazole, methyl 4-(2-methyl-3-carboxymethyl-1H-pyrrol-1-yl)-2-propylimidazole-5-carboxylate, methyl 2-butyl-4-[2-(1-oxo-2,2,2-trifluoroethyl)-1H-pyrrol-1-yl]imidazole-5-carboxylate, methyl 2-propyl-4-(2,5-dichloro-1H-pyrrol-1-yl)imidazole-5-carboxylate, 5-(hydroxymethyl)-2-propyl-4-(1H-pyrrol-1-yl)imidazole, methyl 4-amino-2-cyclopropylimidazole-5-carboxylate, 5-(hydroxymethyl)-2-propyl-4-(2,5-dimethyl-1H-pyrrol-1-yl)imidazole, and methyl (E)-3-[4-(2,5-dimethyl-1H-pyrrol-1-yl)-2-propylimidazol-5-yl]-2-propenoic acid.

* * * * *